United States Patent [19]

Hosein et al.

[11] Patent Number: 5,736,321
[45] Date of Patent: Apr. 7, 1998

[54] PEPTIDES EFFECTIVE FOR DIAGNOSIS AND DETECTION OF HEPATITIS C INFECTION

[75] Inventors: Barbara Helen Hosein, New York; Chang Yi Wang, Cold Spring Harbor, both of N.Y.

[73] Assignee: United Biomedical, Inc., Hauppauge, N.Y.

[21] Appl. No.: 530,550

[22] Filed: Sep. 19, 1995

Related U.S. Application Data

[63] Continuation-in-part of Ser. No. 333,573, Nov. 1, 1994, abandoned.
[51] Int. Cl.$^6$ .................. G01N 33/576; G07K 14/18
[52] U.S. Cl. ............... 435/5; 436/820; 530/350
[58] Field of Search .................. 435/5; 436/820; 530/350

[56] References Cited

U.S. PATENT DOCUMENTS 5,582,968 12/1996 Wang et al. .................. 435/5

*Primary Examiner*—Marian C. Knode
*Assistant Examiner*—Donna C. Wortman
*Attorney, Agent, or Firm*—Morgan & Finnegan, LLP

[57] ABSTRACT

The present invention relates to novel linear and branched peptides specific for the diagnosis and prevention of hepatitis C virus (HCV) infection. More particularly, the present invention is directed to linear and branched synthetic peptides containing at least one antigenic site which is effective for detecting HCV-associated antibodies in patients using immunoassay techniques. In some cases, these peptides are also library peptides with degenerate amino acid positions. Preferred mixtures for detection of HCV antibodies are provided as well as a novel spliced peptide useful for blocking the non-specific reactivity of certain NS-3 conformational epitopes.

25 Claims, 3 Drawing Sheets

SEQUENCE LISTING ( 1 ) GENERAL INFORMATION:

( i i i ) NUMBER OF SEQUENCES: 51

( 2 ) INFORMATION FOR SEQ ID NO:1:

( i ) SEQUENCE CHARACTERISTICS:
        ( A ) LENGTH: 44 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

```
Ala  Arg  Pro  Asp  Tyr  Asn  Pro  Pro  Leu  Val  Glu  Thr  Trp  Lys  Lys  Pro
 1              5                        10                        15

Asp  Tyr  Glu  Pro  Pro  Val  Val  His  Gly  Cys  Pro  Leu  Pro  Pro  Pro  Lys
               20                   25                        30

Ser  Pro  Pro  Val  Pro  Pro  Pro  Arg  Lys  Lys  Arg  Thr
          35                   40
```

( 2 ) INFORMATION FOR SEQ ID NO:2:

( i ) SEQUENCE CHARACTERISTICS:
      ( A ) LENGTH: 47 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:2:

```
Ser  Gly  Lys  Pro  Ala  Ile  Ile  Pro  Asp  Arg  Glu  Val  Leu  Tyr  Arg  Glu
 1              5                        10                        15

Phe  Asp  Glu  Met  Glu  Glu  Cys  Ser  Gln  His  Leu  Pro  Tyr  Ile  Glu  Gln
               20                   25                        30

Gly  Met  Met  Leu  Ala  Glu  Gln  Phe  Lys  Gln  Lys  Ala  Leu  Gly  Leu
          35                   40                        45
```

( 2 ) INFORMATION FOR SEQ ID NO:3:

( i ) SEQUENCE CHARACTERISTICS:
      ( A ) LENGTH: 61 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:3:

```
Ser  Thr  Ile  Pro  Lys  Pro  Gln  Arg  Lys  Thr  Lys  Arg  Asn  Thr  Asn  Arg
 1              5                        10                        15

Arg  Pro  Gln  Asp  Val  Lys  Phe  Pro  Gly  Gly  Gly  Gln  Ile  Val  Gly  Gly
               20                   25                        30

Val  Tyr  Leu  Leu  Pro  Arg  Arg  Gly  Pro  Arg  Leu  Gly  Val  Arg  Ala  Thr
          35                   40                        45

Arg  Lys  Thr  Ser  Glu  Arg  Ser  Gln  Pro  Arg  Gly  Arg  Arg
     50                   55                        60
```

( 2 ) INFORMATION FOR SEQ ID NO:4:

( i ) SEQUENCE CHARACTERISTICS:
      ( A ) LENGTH: 81 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:4:

```
Lys  Ala  Ile  Pro  Leu  Glu  Val  Ile  Lys  Gly  Gly  Arg  His  Leu  Ile  Phe
 1              5                        10                        15

Cys  His  Ser  Lys  Lys  Lys  Cys  Asp  Glu  Leu  Ala  Ala  Lys  Leu  Val  Ala
               20                   25                        30

Leu  Gly  Ile  Asn  Ala  Val  Ala  Tyr  Tyr  Arg  Gly  Leu  Asp  Val  Ser  Val
          35                   40                        45

Ile  Pro  Thr  Ser  Gly  Asp  Val  Val  Val  Ala  Thr  Asp  Ala  Leu  Met
     50                   55                        60

Thr  Gly  Tyr  Thr  Gly  Asp  Phe  Asp  Ser  Val  Ile  Asp  Cys  Asn  Thr  Cys
```

| 65 | | 70 | 75 | 80 |

Val (2) INFORMATION FOR SEQ ID NO:5:

(i) SEQUENCE CHARACTERISTICS:
        (A) LENGTH: 75 amino acids
        (B) TYPE: amino acid
        (D) TOPOLOGY: linear (ii) MOLECULE TYPE: peptide (xi) SEQUENCE DESCRIPTION: SEQ ID NO:5:

```
Lys Lys Lys Lys Ala Ile Pro Leu Glu Val Ile Lys Gly Gly Lys His
  1               5                  10                  15
Leu Ile Phe Cys His Ser Lys Lys Lys Cys Asp Glu Leu Ala Ala Lys
             20                  25                  30
Leu Val Ala Leu Gly Ile Asn Ala Val Ala Tyr Tyr Lys Gly Leu Asp
         35                  40                  45
Val Ser Val Ile Pro Thr Ser Gly Asp Thr Asp Ala Leu Met Thr Gly
     50                  55                  60
Tyr Thr Gly Asp Phe Asp Ser Val Ile Asp Cys
 65              70                  75
```

(2) INFORMATION FOR SEQ ID NO:6:

(i) SEQUENCE CHARACTERISTICS:
        (A) LENGTH: 77 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /note= "Norvaline"

(ix) FEATURE:
        (A) NAME/KEY: Modified-site
        (B) LOCATION: 7
        (D) OTHER INFORMATION: /note= "Norvaline"

(ix) FEATURE:
        (A) NAME/KEY: Modified-site
        (B) LOCATION: 16
        (D) OTHER INFORMATION: /note= "Norvaline"

(xi) SEQUENCE DESCRIPTION: SEQ ID NO:6:

```
Lys Ala Xaa Pro Leu Glu Xaa Val Lys Gly Gly Arg His Leu Ile Xaa
  1               5                  10                  15
Cys His Thr Lys Lys Lys Cys Asp Glu Leu Ala Ala Lys Leu Val Ala
             20                  25                  30
Leu Gly Ile Asn Ala Val Ala Tyr Tyr Arg Gly Leu Asp Val Ser Val
         35                  40                  45
Ile Pro Thr Ser Gly Asp Val Val Val Ala Thr Asp Ala Leu Met
     50                  55                  60
Thr Gly Tyr Thr Gly Asp Phe Asp Ser Val Ile Asp Cys
 65              70                  75
```

(2) INFORMATION FOR SEQ ID NO:7:

(i) SEQUENCE CHARACTERISTICS:
        (A) LENGTH: 81 amino acids
        (B) TYPE: amino acid
        (D) TOPOLOGY: linear ( i i ) MOLECULE TYPE: peptide ( i x ) FEATURE:
    ( A ) NAME/KEY: Modified-site
    ( B ) LOCATION: 3
    ( D ) OTHER INFORMATION: /note= "Norvaline"

( i x ) FEATURE:
    ( A ) NAME/KEY: Modified-site
    ( B ) LOCATION: 7
    ( D ) OTHER INFORMATION: /note= "Norvaline"

( i x ) FEATURE:
    ( A ) NAME/KEY: Modified-site
    ( B ) LOCATION: 16
    ( D ) OTHER INFORMATION: /note= "Norvaline"

( i x ) FEATURE:
    ( A ) NAME/KEY: Modified-site
    ( B ) LOCATION: 26
    ( D ) OTHER INFORMATION: /note= "Norleucine"

( i x ) FEATURE:
    ( A ) NAME/KEY: Modified-site
    ( B ) LOCATION: 31
    ( D ) OTHER INFORMATION: /note= "Norvaline"

( x i ) SEQUENCE DESCRIPTION: SEQ ID NO:7:

```
Lys Ala Xaa Pro Leu Glu Xaa Val Lys Gly Gly Arg His Leu Ile Xaa
 1               5                  10                      15

Cys His Thr Lys Lys Lys Cys Asp Glu Xaa Ala Ala Lys Leu Xaa Ala
             20              25                      30

Leu Gly Ile Asn Ala Val Ala Tyr Tyr Arg Gly Leu Asp Val Ser Val
             35              40                      45

Ile Pro Thr Ser Gly Asp Val Val Val Ala Thr Asp Ala Leu Met
     50              55                      60

Thr Gly Tyr Thr Gly Asp Phe Asp Ser Val Ile Asp Cys Asn Thr Cys
 65              70                      75                  80

Val
```

( 2 ) INFORMATION FOR SEQ ID NO:8:

( i ) SEQUENCE CHARACTERISTICS:
        ( A ) LENGTH: 81 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 3
        ( D ) OTHER INFORMATION: /note= "Norvaline"

( i x ) FEATURE:
        ( A ) NAME/KEY: Modified-site
        ( B ) LOCATION: 7
        ( D ) OTHER INFORMATION: /note= "Norvaline"

( i x ) FEATURE:
        ( A ) NAME/KEY: Modified-site
        ( B ) LOCATION: 16
        ( D ) OTHER INFORMATION: /note= "Norvaline"

( i x ) FEATURE:
        ( A ) NAME/KEY: Modified-site
        ( B ) LOCATION: 26
        ( D ) OTHER INFORMATION: /note= "Norleucine"

( i x ) FEATURE:
        ( A ) NAME/KEY: Modified-site
        ( B ) LOCATION: 38

( D ) OTHER INFORMATION: /note= "Norvaline"

( x i ) SEQUENCE DESCRIPTION: SEQ ID NO:8:

| Lys | Ala | Xaa | Pro | Leu | Glu | Xaa | Val | Lys | Gly | Gly | Arg | His | Leu | Ile | Xaa |
|---|---|---|---|---|---|---|---|---|---|---|---|---|---|---|---|
| 1 | | | | 5 | | | | | 10 | | | | | 15 | |
| Cys | His | Ala | Lys | Lys | Lys | Cys | Asp | Glu | Xaa | Ala | Ala | Lys | Leu | Val | Ala |
| | | | 20 | | | | | 25 | | | | | 30 | | |
| Leu | Gly | Ile | Asn | Ala | Xaa | Ala | Tyr | Tyr | Arg | Gly | Leu | Asp | Val | Ser | Val |
| | | | 35 | | | | 40 | | | | | 45 | | | |
| Ile | Pro | Thr | Ser | Gly | Asp | Val | Val | Val | Ala | Thr | Asp | Ala | Leu | Met | |
| | 50 | | | | | 55 | | | | 60 | | | | | |
| Thr | Gly | Tyr | Thr | Gly | Asp | Phe | Asp | Ser | Val | Ile | Asp | Cys | Asn | Thr | Cys |
| 65 | | | | | 70 | | | | | 75 | | | | | 80 |
| Val | | | | | | | | | | | | | | | |

( 2 ) INFORMATION FOR SEQ ID NO:9:

( i ) SEQUENCE CHARACTERISTICS:
    ( A ) LENGTH: 81 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 3
    ( D ) OTHER INFORMATION: /note= "Norvaline"

( i x ) FEATURE:
    ( A ) NAME/KEY: Modified-site
    ( B ) LOCATION: 7
    ( D ) OTHER INFORMATION: /note=
      " V0.30;A0.30;T0.10;F0.10;Y0.10;Norvaline0.10"

( i x ) FEATURE:
    ( A ) NAME/KEY: Modified-site
    ( B ) LOCATION: 38
    ( D ) OTHER INFORMATION: /note= "Norvaline"

( i x ) FEATURE:
    ( A ) NAME/KEY: Modified-site
    ( B ) LOCATION: 46
    ( D ) OTHER INFORMATION: /note= "Norvaline"

( x i ) SEQUENCE DESCRIPTION: SEQ ID NO:9:

| Lys | Ala | Xaa | Pro | Leu | Glu | Val | Val | Lys | Gly | Gly | Arg | His | Leu | Ile | Phe |
|---|---|---|---|---|---|---|---|---|---|---|---|---|---|---|---|
| 1 | | | | 5 | | | | | 10 | | | | | 15 | |
| Cys | His | Ser | Lys | Lys | Lys | Cys | Asp | Glu | Leu | Ala | Ala | Lys | Leu | Val | Ala |
| | | | 20 | | | | | 25 | | | | | 30 | | |
| Leu | Gly | Ile | Asn | Ala | Xaa | Ala | Tyr | Tyr | Arg | Gly | Leu | Asp | Xaa | Ser | Val |
| | | | 35 | | | | 40 | | | | | 45 | | | |
| Ile | Pro | Thr | Ser | Gly | Asp | Val | Val | Val | Ala | Thr | Asp | Ala | Leu | Met | |
| | 50 | | | | | 55 | | | | 60 | | | | | |
| Thr | Gly | Tyr | Thr | Gly | Asp | Phe | Asp | Ser | Val | Ile | Asp | Cys | Asn | Thr | Cys |
| 65 | | | | | 70 | | | | | 75 | | | | | 80 |
| Val | | | | | | | | | | | | | | | |

( 2 ) INFORMATION FOR SEQ ID NO:10:

( i ) SEQUENCE CHARACTERISTICS:
    ( A ) LENGTH: 81 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 3
    ( D ) OTHER INFORMATION: /note= "Norvaline"

( i x ) FEATURE:
    ( A ) NAME/KEY: Modified-site
    ( B ) LOCATION: 7
    ( D ) OTHER INFORMATION: /note=
        " V0.30;A0.30;T0.10;F0.10;Y0.10;Norvaline0.10"

( x i ) SEQUENCE DESCRIPTION: SEQ ID NO:10:

```
Lys  Ala  Xaa  Pro  Leu  Glu  Val  Val  Lys  Gly  Gly  Arg  His  Leu  Ile  Phe
 1              5                        10                            15

Cys  His  Ser  Lys  Lys  Lys  Cys  Asp  Glu  Leu  Ala  Ala  Lys  Leu  Val  Ala
              20                        25                        30

Leu  Gly  Ile  Asn  Ala  Val  Ala  Tyr  Tyr  Arg  Gly  Leu  Asp  Val  Ser  Val
              35                        40                        45

Ile  Pro  Thr  Ser  Gly  Asp  Val  Val  Val  Ala  Thr  Asp  Ala  Leu  Met
         50                        55                        60

Thr  Gly  Tyr  Thr  Gly  Glu  Phe  Asp  Ser  Val  Ile  Asp  Cys  Asn  Thr  Cys
65                       70                        75                       80

Val
```

( 2 ) INFORMATION FOR SEQ ID NO:11:

( i ) SEQUENCE CHARACTERISTICS:
        ( A ) LENGTH: 81 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 3
        ( D ) OTHER INFORMATION: /note= "Norvaline"

( i x ) FEATURE:
        ( A ) NAME/KEY: Modified-site
        ( B ) LOCATION: 7
        ( D ) OTHER INFORMATION: /note=
            " V0.30;A0.30;T0.10;F0.10;Y0.10;Norvaline0.10"

( i x ) FEATURE:
        ( A ) NAME/KEY: Modified-site
        ( B ) LOCATION: 16
        ( D ) OTHER INFORMATION: /note= "Norvaline"

( i x ) FEATURE:
        ( A ) NAME/KEY: Modified-site
        ( B ) LOCATION: 26
        ( D ) OTHER INFORMATION: /note= "Norleucine"

( i x ) FEATURE:
        ( A ) NAME/KEY: Modified-site
        ( B ) LOCATION: 46
        ( D ) OTHER INFORMATION: /note= "Norvaline"

( i x ) FEATURE:
        ( A ) NAME/KEY: Modified-site
        ( B ) LOCATION: 74
        ( D ) OTHER INFORMATION: /note= "Norvaline"

( x i ) SEQUENCE DESCRIPTION: SEQ ID NO:11:

```
Lys  Ala  Xaa  Pro  Leu  Glu  Val  Val  Lys  Gly  Gly  Arg  His  Leu  Ile  Xaa
 1              5                        10                            15

Cys  His  Ser  Lys  Lys  Lys  Cys  Asp  Glu  Xaa  Ala  Ala  Lys  Leu  Val  Ala
              20                        25                        30
```

|   |   |   |   |   |   |   |   |   |   |   |   |   |   |   |
|---|---|---|---|---|---|---|---|---|---|---|---|---|---|---|
| Leu | Gly | Ile<br>35 | Gln | Ala | Val | Ala | Tyr<br>40 | Tyr | Arg | Gly | Leu | Asp<br>45 | Xaa | Ser | Val |
| Ile | Pro<br>50 | Thr | Ser | Gly | Asp | Val<br>55 | Val | Val | Val | Ala | Thr<br>60 | Asp | Ala | Leu | Met |
| Thr<br>65 | Gly | Tyr | Thr | Gly | Asp<br>70 | Phe | Asp | Ser | Xaa | Ile<br>75 | Asp | Cys | Asn | Thr | Cys<br>80 |
| Val |

( 2 ) INFORMATION FOR SEQ ID NO:12:

( i ) SEQUENCE CHARACTERISTICS:
        ( A ) LENGTH: 81 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 3
        ( D ) OTHER INFORMATION: /note= "Norvaline"

( i x ) FEATURE:
        ( A ) NAME/KEY: Modified-site
        ( B ) LOCATION: 7
        ( D ) OTHER INFORMATION: /note=
            " V0.30;A0.30;T0.10;F0.10;Y0.10;Norvaline0.10"

( i x ) FEATURE:
        ( A ) NAME/KEY: Modified-site
        ( B ) LOCATION: 63
        ( D ) OTHER INFORMATION: /note= "Norleucine"

( x i ) SEQUENCE DESCRIPTION: SEQ ID NO:12:

|   |   |   |   |   |   |   |   |   |   |   |   |   |   |   |   |
|---|---|---|---|---|---|---|---|---|---|---|---|---|---|---|---|
| Lys<br>1 | Ala | Xaa | Pro | Leu<br>5 | Glu | Val | Val | Lys | Gly<br>10 | Gly | Arg | His | Leu | Ile<br>15 | Phe |
| Cys | His | Ser | Lys<br>20 | Lys | Lys | Cys | Asp | Glu<br>25 | Leu | Ala | Ala | Lys | Leu<br>30 | Val | Ala |
| Leu | Gly | Ile<br>35 | Asn | Ala | Val | Ala | Tyr<br>40 | Tyr | Arg | Gly | Leu | Asp<br>45 | Val | Ser | Val |
| Ile | Pro<br>50 | Thr | Ser | Gly | Asp | Val<br>55 | Val | Val | Val | Ala | Thr<br>60 | Asp | Ala | Xaa | Met |
| Thr<br>65 | Gly | Tyr | Thr | Gly | Asp<br>70 | Phe | Glu | Ser | Val | Ile<br>75 | Asp | Cys | Asn | Thr | Cys<br>80 |
| Val |

( 2 ) INFORMATION FOR SEQ ID NO:13:

( i ) SEQUENCE CHARACTERISTICS:
        ( A ) LENGTH: 81 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 3
        ( D ) OTHER INFORMATION: /note= "Norvaline"

( i x ) FEATURE:
        ( A ) NAME/KEY: Modified-site
        ( B ) LOCATION: 7
        ( D ) OTHER INFORMATION: /note=
            " V0.30;A0.30;T0.10;F0.10;Y0.10;Norvaline0.10"

( i x ) FEATURE:
        ( A ) NAME/KEY: Modified-site
        ( B ) LOCATION: 16

-continued ( D ) OTHER INFORMATION: /note= "Norvaline"

( i x ) FEATURE:
    ( A ) NAME/KEY: Modified-site
    ( B ) LOCATION: 26
    ( D ) OTHER INFORMATION: /note= "Norleucine"

( i x ) FEATURE:
    ( A ) NAME/KEY: Modified-site
    ( B ) LOCATION: 46
    ( D ) OTHER INFORMATION: /note= "Norvaline"

( i x ) FEATURE:
    ( A ) NAME/KEY: Modified-site
    ( B ) LOCATION: 50
    ( D ) OTHER INFORMATION: /note= "Hydroxyproline"

( i x ) FEATURE:
    ( A ) NAME/KEY: Modified-site
    ( B ) LOCATION: 63
    ( D ) OTHER INFORMATION: /note= "Norleucine"

( x i ) SEQUENCE DESCRIPTION: SEQ ID NO:13:

```
Lys Ala Xaa Pro Leu Glu Val Val Lys Gly Gly Arg His Leu Ile Xaa
1               5                   10                  15
Cys His Ser Lys Lys Lys Cys Asp Glu Xaa Ala Ala Lys Leu Val Ala
            20                  25                  30
Leu Gly Ile Asn Ala Val Ala Tyr Tyr Arg Gly Leu Asp Xaa Ser Val
            35                  40                  45
Ile Pro Thr Ala Gly Asp Val Val Val Ala Thr Asp Ala Xaa Met
    50                  55                  60
Thr Gly Tyr Thr Gly Asp Phe Asp Ser Val Ile Asp Cys Asn Thr Cys
65                  70                  75                  80
Val
```

( 2 ) INFORMATION FOR SEQ ID NO:14:

( i ) SEQUENCE CHARACTERISTICS:
        ( A ) LENGTH: 81 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 3
        ( D ) OTHER INFORMATION: /note= "Norvaline"

( i x ) FEATURE:
        ( A ) NAME/KEY: Modified-site
        ( B ) LOCATION: 7
        ( D ) OTHER INFORMATION: /note=
            " V0.30;A0.30;T0.10;F0.10;Y0.10;Norvaline0.10"

( i x ) FEATURE:
        ( A ) NAME/KEY: Modified-site
        ( B ) LOCATION: 16
        ( D ) OTHER INFORMATION: /note= "Norvaline"

( i x ) FEATURE:
        ( A ) NAME/KEY: Modified-site
        ( B ) LOCATION: 26
        ( D ) OTHER INFORMATION: /note= "Norleucine"

( i x ) FEATURE:
        ( A ) NAME/KEY: Modified-site
        ( B ) LOCATION: 35
        ( D ) OTHER INFORMATION: /note= "Norleucine"

( i x ) FEATURE:
        ( A ) NAME/KEY: Modified-site
        ( B ) LOCATION: 44

(D) OTHER INFORMATION: /note= "Norleucine"

(ix) FEATURE:
    (A) NAME/KEY: Modified-site
    (B) LOCATION: 63
    (D) OTHER INFORMATION: /note= "Norleucine"

(xi) SEQUENCE DESCRIPTION: SEQ ID NO:14:

| Lys | Ala | Xaa | Pro | Leu | Glu | Val | Val | Lys | Gly | Gly | Arg | His | Leu | Ile | Xaa |
|---|---|---|---|---|---|---|---|---|---|---|---|---|---|---|---|
| 1 | | | | 5 | | | | | 10 | | | | | 15 | |
| Cys | His | Ser | Lys | Lys | Lys | Cys | Asp | Glu | Xaa | Ala | Ala | Lys | Leu | Val | Ala |
| | | | 20 | | | | | 25 | | | | | 30 | | |
| Leu | Gly | Xaa | Asn | Ala | Val | Ala | Tyr | Tyr | Arg | Gly | Xaa | Asp | Val | Ser | Val |
| | | 35 | | | | | 40 | | | | | 45 | | | |
| Ile | Pro | Thr | Ala | Gly | Asp | Val | Val | Val | Ala | Thr | Asp | Ala | Xaa | Met | |
| | 50 | | | | | 55 | | | | | | 60 | | | |
| Thr | Gly | Tyr | Thr | Gly | Asp | Phe | Asp | Ser | Val | Ile | Asp | Cys | Asn | Thr | Cys |
| 65 | | | | | 70 | | | | | 75 | | | | | 80 |
| Val | | | | | | | | | | | | | | | |

(2) INFORMATION FOR SEQ ID NO:15:

(i) SEQUENCE CHARACTERISTICS:
        (A) LENGTH: 81 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /note= "Norvaline"

(ix) FEATURE:
        (A) NAME/KEY: Modified-site
        (B) LOCATION: 7
        (D) OTHER INFORMATION: /note=
            " V0.30;A0.30;T0.10;F0.10;Y0.10;Norvaline0.10"

(ix) FEATURE:
        (A) NAME/KEY: Modified-site
        (B) LOCATION: 16
        (D) OTHER INFORMATION: /note= "Norvaline"

(ix) FEATURE:
        (A) NAME/KEY: Modified-site
        (B) LOCATION: 26
        (D) OTHER INFORMATION: /note= "Norleucine"

(ix) FEATURE:
        (A) NAME/KEY: Modified-site
        (B) LOCATION: 46
        (D) OTHER INFORMATION: /note= "Norvaline"

(ix) FEATURE:
        (A) NAME/KEY: Modified-site
        (B) LOCATION: 63
        (D) OTHER INFORMATION: /note= "Norleucine"

(ix) FEATURE:
        (A) NAME/KEY: Modified-site
        (B) LOCATION: 74
        (D) OTHER INFORMATION: /note= "Norvaline"

(xi) SEQUENCE DESCRIPTION: SEQ ID NO:15:

| Lys | Ala | Xaa | Pro | Leu | Glu | Val | Val | Lys | Gly | Gly | Arg | His | Leu | Ile | Xaa |
|---|---|---|---|---|---|---|---|---|---|---|---|---|---|---|---|
| 1 | | | | 5 | | | | | 10 | | | | | 15 | |
| Cys | His | Ser | Lys | Lys | Lys | Cys | Asp | Glu | Xaa | Ala | Ala | Lys | Leu | Val | Ala |
| | | | 20 | | | | | 25 | | | | | 30 | | |

```
Leu Gly Ile Asn Ala Val Ala Tyr Tyr Arg Gly Leu Asp Xaa Ser Val
        35                  40                    45

Ile Pro Thr Ala Gly Asp Val Val Val Ala Thr Asp Ala Xaa Met
    50              55                  60

Thr Gly Tyr Ser Gly Asp Phe Asp Ser Xaa Ile Asp Cys Asn Thr Cys
65                  70                  75                      80

Val
```

( 2 ) INFORMATION FOR SEQ ID NO:16:

( i ) SEQUENCE CHARACTERISTICS:
        ( A ) LENGTH: 81 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 3
        ( D ) OTHER INFORMATION: /note= "Norvaline"

( i x ) FEATURE:
        ( A ) NAME/KEY: Modified-site
        ( B ) LOCATION: 7
        ( D ) OTHER INFORMATION: /note=
            " V0.30;A0.30;T0.10;F0.10;Y0.10;Norvaline0.10"

( i x ) FEATURE:
        ( A ) NAME/KEY: Modified-site
        ( B ) LOCATION: 16
        ( D ) OTHER INFORMATION: /note= "Norvaline"

( i x ) FEATURE:
        ( A ) NAME/KEY: Modified-site
        ( B ) LOCATION: 26
        ( D ) OTHER INFORMATION: /note= "Norleucine"

( i x ) FEATURE:
        ( A ) NAME/KEY: Modified-site
        ( B ) LOCATION: 33
        ( D ) OTHER INFORMATION: /note= "Norleucine"

( i x ) FEATURE:
        ( A ) NAME/KEY: Modified-site
        ( B ) LOCATION: 46
        ( D ) OTHER INFORMATION: /note= "Norvaline"

( i x ) FEATURE:
        ( A ) NAME/KEY: Modified-site
        ( B ) LOCATION: 63
        ( D ) OTHER INFORMATION: /note= "Norleucine"

( i x ) FEATURE:
        ( A ) NAME/KEY: Modified-site
        ( B ) LOCATION: 74
        ( D ) OTHER INFORMATION: /note= "Norvaline"

( x i ) SEQUENCE DESCRIPTION: SEQ ID NO:16:

```
Lys Ala Xaa Pro Leu Glu Val Val Lys Gly Gly Arg His Leu Ile Xaa
1               5                   10                      15

Cys His Ser Lys Lys Lys Cys Asp Glu Xaa Ala Ala Lys Leu Val Ala
            20                  25                  30

Xaa Gly Ile Asn Ser Val Ala Tyr Tyr Arg Gly Leu Asp Xaa Ser Val
        35                  40                  45

Ile Pro Thr Ala Gly Asp Val Val Val Ala Ser Asp Ala Xaa Met
    50              55                  60

Thr Gly Tyr Ser Gly Asp Phe Asp Ser Xaa Ile Asp Cys Asn Thr Cys
65                  70                  75                      80

Val
```

( 2 ) INFORMATION FOR SEQ ID NO:17:

( i ) SEQUENCE CHARACTERISTICS:
        ( A ) LENGTH: 81 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 3
        ( D ) OTHER INFORMATION: /note= "Norvaline"

( i x ) FEATURE:
        ( A ) NAME/KEY: Modified-site
        ( B ) LOCATION: 7
        ( D ) OTHER INFORMATION: /note=
            " V0.30;A0.30;T0.10;F0.10;Y0.10;Norvaline0.10"

( i x ) FEATURE:
        ( A ) NAME/KEY: Modified-site
        ( B ) LOCATION: 16
        ( D ) OTHER INFORMATION: /note= "Norvaline"

( i x ) FEATURE:
        ( A ) NAME/KEY: Modified-site
        ( B ) LOCATION: 26
        ( D ) OTHER INFORMATION: /note= "Norleucine"

( i x ) FEATURE:
        ( A ) NAME/KEY: Modified-site
        ( B ) LOCATION: 33
        ( D ) OTHER INFORMATION: /note= "Norleucine"

( i x ) FEATURE:
        ( A ) NAME/KEY: Modified-site
        ( B ) LOCATION: 46
        ( D ) OTHER INFORMATION: /note= "Norvaline"

( i x ) FEATURE:
        ( A ) NAME/KEY: Modified-site
        ( B ) LOCATION: 63
        ( D ) OTHER INFORMATION: /note= "Norleucine"

( i x ) FEATURE:
        ( A ) NAME/KEY: Modified-site
        ( B ) LOCATION: 74
        ( D ) OTHER INFORMATION: /note= "Norvaline"

( x i ) SEQUENCE DESCRIPTION: SEQ ID NO:17:

```
Lys Ala Xaa Pro Leu Glu Val Val Lys Gly Gly Arg His Leu Ile Xaa
1                5                   10                          15

Cys His Ser Lys Lys Lys Cys Asp Glu Xaa Ala Ala Lys Leu Val Ala
            20                  25                      30

Xaa Gly Ile Asn Ala Ile Ala Tyr Tyr Arg Gly Leu Asp Xaa Ser Val
        35                  40                      45

Ile Pro Thr Ala Gly Asp Val Val Val Ala Ser Asp Ala Xaa Met
    50                  55                      60

Thr Gly Tyr Ser Gly Asp Phe Asp Ser Xaa Ile Asp Cys Asn Thr Cys
65                  70                  75                      80

Val
```

( 2 ) INFORMATION FOR SEQ ID NO:18:

( i ) SEQUENCE CHARACTERISTICS:
        ( A ) LENGTH: 81 amino acids
        ( B ) TYPE: amino acid
        ( D ) TOPOLOGY: linear ( i i ) MOLECULE TYPE: peptide ( i x ) FEATURE:
  ( A ) NAME/KEY: Modified-site
  ( B ) LOCATION: 3
  ( D ) OTHER INFORMATION: /note= "Norvaline"

( i x ) FEATURE:
  ( A ) NAME/KEY: Modified-site
  ( B ) LOCATION: 3
  ( D ) OTHER INFORMATION: /note=
    " V0.30;A0.30;T0.10;F0.10;Y0.10;Norvaline0.10"

( i x ) FEATURE:
  ( A ) NAME/KEY: Modified-site
  ( B ) LOCATION: 16
  ( D ) OTHER INFORMATION: /note= "Norvaline"

( i x ) FEATURE:
  ( A ) NAME/KEY: Modified-site
  ( B ) LOCATION: 26
  ( D ) OTHER INFORMATION: /note= "Norleucine"

( i x ) FEATURE:
  ( A ) NAME/KEY: Modified-site
  ( B ) LOCATION: 33
  ( D ) OTHER INFORMATION: /note= "Norleucine"

( i x ) FEATURE:
  ( A ) NAME/KEY: Modified-site
  ( B ) LOCATION: 46
  ( D ) OTHER INFORMATION: /note= "Norvaline"

( i x ) FEATURE:
  ( A ) NAME/KEY: Modified-site
  ( B ) LOCATION: 63
  ( D ) OTHER INFORMATION: /note= "Norleucine"

( i x ) FEATURE:
  ( A ) NAME/KEY: Modified-site
  ( B ) LOCATION: 74
  ( D ) OTHER INFORMATION: /note= "Norvaline"

( x i ) SEQUENCE DESCRIPTION: SEQ ID NO:18:

```
Lys Ala Xaa Pro Leu Glu Val Val Lys Gly Gly Arg His Leu Ile Xaa
 1               5                   10                  15

Cys His Ser Lys Lys Lys Cys Glu Glu Xaa Ala Ala Lys Leu Val Ala
             20                  25                  30

Xaa Gly Ile Asn Ala Val Ser Tyr Tyr Arg Gly Leu Asp Xaa Ser Val
         35                  40                  45

Ile Pro Thr Ala Gly Asp Val Val Val Ala Ser Asp Ala Xaa Met
     50                  55                  60

Thr Gly Tyr Ser Gly Asp Phe Asp Ser Xaa Ile Asp Cys Asn Thr Cys
65                      70                  75                  80

Val
```

( 2 ) INFORMATION FOR SEQ ID NO:19:

( i ) SEQUENCE CHARACTERISTICS:
    ( A ) LENGTH: 81 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 3
    ( D ) OTHER INFORMATION: /note= "Norvaline"

( i x ) FEATURE:
    ( A ) NAME/KEY: Modified-site
    ( B ) LOCATION: 7
    ( D ) OTHER INFORMATION: /note=

"V0.30;A0.30;T0.10;F0.10;Y0.10;Norvaline0.10"

( i x ) FEATURE:
    ( A ) NAME/KEY: Modified-site
    ( B ) LOCATION: 16
    ( D ) OTHER INFORMATION: /note= "Norvaline"

( i x ) FEATURE:
    ( A ) NAME/KEY: Modified-site
    ( B ) LOCATION: 26
    ( D ) OTHER INFORMATION: /note= "Norleucine"

( i x ) FEATURE:
    ( A ) NAME/KEY: Modified-site
    ( B ) LOCATION: 33
    ( D ) OTHER INFORMATION: /note= "Norleucine"

( i x ) FEATURE:
    ( A ) NAME/KEY: Modified-site
    ( B ) LOCATION: 46
    ( D ) OTHER INFORMATION: /note= "Norvaline"

( i x ) FEATURE:
    ( A ) NAME/KEY: Modified-site
    ( B ) LOCATION: 63
    ( D ) OTHER INFORMATION: /note= "Norleucine"

( i x ) FEATURE:
    ( A ) NAME/KEY: Modified-site
    ( B ) LOCATION: 74
    ( D ) OTHER INFORMATION: /note= "Norvaline"

( x i ) SEQUENCE DESCRIPTION: SEQ ID NO:19:

```
Lys Ala Xaa Pro Leu Glu Val Val Lys Gly Gly Arg His Leu Ile Xaa
1               5                   10                      15

Cys His Ser Arg Lys Lys Cys Asp Glu Xaa Ala Ala Lys Leu Val Ala
            20                  25                  30

Xaa Gly Ile Asn Ala Val Ser Tyr Tyr Arg Gly Leu Asp Xaa Ser Val
        35                  40                  45

Ile Pro Thr Ala Gly Asp Val Val Val Ala Ser Asp Ala Xaa Met
    50              55                  60

Thr Gly Tyr Ser Gly Asp Phe Asp Ser Xaa Ile Asp Cys Asn Thr Cys
65              70                  75                      80

Val
```

( 2 ) INFORMATION FOR SEQ ID NO:20:

( i ) SEQUENCE CHARACTERISTICS:
        ( A ) LENGTH: 81 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 3
        ( D ) OTHER INFORMATION: /note= "Norvaline"

( i x ) FEATURE:
        ( A ) NAME/KEY: Modified-site
        ( B ) LOCATION: 7
        ( D ) OTHER INFORMATION: /note=
            "V0.30;A0.30;T0.10;F0.10;Y0.10;Norvaline0.10"

( i x ) FEATURE:
        ( A ) NAME/KEY: Modified-site
        ( B ) LOCATION: 16
        ( D ) OTHER INFORMATION: /note= "Norvaline"

( i x ) FEATURE:
        ( A ) NAME/KEY: Modified-site
        ( B ) LOCATION: 26

( D ) OTHER INFORMATION: /note= "Norleucine"

( i x ) FEATURE:
    ( A ) NAME/KEY: Modified-site
    ( B ) LOCATION: 33
    ( D ) OTHER INFORMATION: /note= "Norleucine"

( i x ) FEATURE:
    ( A ) NAME/KEY: Modified-site
    ( B ) LOCATION: 46
    ( D ) OTHER INFORMATION: /note= "Norvaline"

( i x ) FEATURE:
    ( A ) NAME/KEY: Modified-site
    ( B ) LOCATION: 63
    ( D ) OTHER INFORMATION: /note= "Norleucine"

( i x ) FEATURE:
    ( A ) NAME/KEY: Modified-site
    ( B ) LOCATION: 74
    ( D ) OTHER INFORMATION: /note= "Norvaline"

( x i ) SEQUENCE DESCRIPTION: SEQ ID NO:20:

```
Lys Ala Xaa Pro Leu Glu Val Xaa Lys Gly Gly Arg His Leu Ile Xaa
1               5                   10                  15
Cys His Ser Arg Lys Lys Cys Asp Glu Xaa Ala Ala Lys Leu Val Ala
            20                  25                  30
Xaa Gly Ile Asn Ala Val Ser Tyr Tyr Arg Gly Leu Asp Xaa Ser Val
            35                  40                  45
Ile Pro Thr Ala Gly Asp Val Val Val Ala Ser Asp Ala Xaa Met
        50                  55                  60
Thr Gly Tyr Ser Gly Asp Phe Asp Ser Xaa Ile Asp Cys Asn Thr Cys
65                      70                  75                  80
Val
```

( 2 ) INFORMATION FOR SEQ ID NO:21:

( i ) SEQUENCE CHARACTERISTICS:
        ( A ) LENGTH: 84 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:21:

```
Lys Lys Lys Lys Ala Ile Pro Leu Glu Val Ile Lys Gly Gly Arg His
1               5                   10                  15
Leu Ile Phe Cys His Ser Arg Arg Arg Cys Asp Glu Leu Ala Ala Lys
            20                  25                  30
Leu Val Ala Leu Gly Ile Asn Ala Val Ala Tyr Tyr Arg Gly Leu Asp
            35                  40                  45
Val Ser Val Ile Pro Thr Ser Gly Asp Val Val Val Ala Thr Asp
    50                  55                  60
Ala Leu Met Thr Gly Tyr Thr Gly Asp Phe Asp Ser Val Ile Asp Cys
65                      70                  75                  80
Asn Thr Cys Val
```

( 2 ) INFORMATION FOR SEQ ID NO:22:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:22:

```
Val Lys Phe Pro Gly Gly Gly Gln Ile Met
1               5                   10
```

( 2 ) INFORMATION FOR SEQ ID NO:23:

( i ) SEQUENCE CHARACTERISTICS:
        ( A ) LENGTH: 62 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 9
        ( D ) OTHER INFORMATION: /note= "Ornithine"

( i x ) FEATURE:
        ( A ) NAME/KEY: Modified-site
        ( B ) LOCATION: 22
        ( D ) OTHER INFORMATION: /note= "Norvaline"

( i x ) FEATURE:
        ( A ) NAME/KEY: Modified-site
        ( B ) LOCATION: 31
        ( D ) OTHER INFORMATION: /note= "Norvaline"

( i x ) FEATURE:
        ( A ) NAME/KEY: Modified-site
        ( B ) LOCATION: 44
        ( D ) OTHER INFORMATION: /note= "Norleucine"

( i x ) FEATURE:
        ( A ) NAME/KEY: Modified-site
        ( B ) LOCATION: 58
        ( D ) OTHER INFORMATION: /note= "Hydroxyproline"

( x i ) SEQUENCE DESCRIPTION: SEQ ID NO:23:

```
Lys Lys Lys Ile Pro Lys Pro Asn Xaa Lys Thr Lys Arg Asn Thr Gln
1               5                   10                  15

Arg Arg Pro Asn Asp Xaa Lys Phe Pro Gly Gly Gly Asn Ile Xaa Gly
                20              25                  30

Gly Val Tyr Leu Val Pro Arg Arg Gly Pro Arg Xaa Gly Leu Arg Ala
            35              40              45

Thr Arg Lys Thr Thr Glu Arg Ser Gln Xaa Arg Gly Arg Arg
    50              55              60
```

( 2 ) INFORMATION FOR SEQ ID NO:24:

( i ) SEQUENCE CHARACTERISTICS:
        ( A ) LENGTH: 64 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 7
        ( D ) OTHER INFORMATION: /note= "P0.90;G0.10"

( i x ) FEATURE:
        ( A ) NAME/KEY: Modified-site
        ( B ) LOCATION: 11
        ( D ) OTHER INFORMATION: /note= "Ornithine"

( i x ) FEATURE:
        ( A ) NAME/KEY: Modified-site
        ( B ) LOCATION: 13
        ( D ) OTHER INFORMATION: /note= "T0.70;N0.30"

( i x ) FEATURE:

(A) NAME/KEY: Modified-site
(B) LOCATION: 24
(D) OTHER INFORMATION: /note= "Norvaline"

(ix) FEATURE:
(A) NAME/KEY: Modified-site
(B) LOCATION: 33
(D) OTHER INFORMATION: /note= "Norvaline"

(ix) FEATURE:
(A) NAME/KEY: Modified-site
(B) LOCATION: 39
(D) OTHER INFORMATION: /note= "Norleucine"

(ix) FEATURE:
(A) NAME/KEY: Modified-site
(B) LOCATION: 46
(D) OTHER INFORMATION: /note= "Norleucine"

(ix) FEATURE:
(A) NAME/KEY: Modified-site
(B) LOCATION: 51
(D) OTHER INFORMATION: /note= "T0.90;P0.10"

(ix) FEATURE:
(A) NAME/KEY: Modified-site
(B) LOCATION: 60
(D) OTHER INFORMATION: /note= "Hydroxyproline"

(xi) SEQUENCE DESCRIPTION: SEQ ID NO:24:

```
Lys Lys Lys Ser Thr Ile Pro Lys Pro Gln Xaa Lys Thr Lys Arg Asn
1               5                   10                  15

Thr Asn Lys Arg Pro Gln Asp Xaa Lys Phe Pro Gly Gly Gly Gln Ile
            20                  25                  30

Xaa Gly Gly Val Tyr Leu Xaa Pro Arg Arg Gly Pro Arg Xaa Gly Leu
        35                  40                  45

Arg Ala Thr Arg Lys Thr Thr Glu Arg Ser Gln Xaa Arg Gly Arg Arg
    50                  55                  60
```

(2) INFORMATION FOR SEQ ID NO:25:

(i) SEQUENCE CHARACTERISTICS:
(A) LENGTH: 64 amino acids
(B) TYPE: amino acid
(D) TOPOLOGY: linear (ii) MOLECULE TYPE: peptide (ix) FEATURE:
(A) NAME/KEY: Modified-site
(B) LOCATION: 7
(D) OTHER INFORMATION: /note= "P0.90;G0.10"

(ix) FEATURE:
(A) NAME/KEY: Modified-site
(B) LOCATION: 11
(D) OTHER INFORMATION: /note= "Ornithine"

(ix) FEATURE:
(A) NAME/KEY: Modified-site
(B) LOCATION: 13
(D) OTHER INFORMATION: /note= "T0.70;N0.30"

(ix) FEATURE:
(A) NAME/KEY: Modified-site
(B) LOCATION: 24
(D) OTHER INFORMATION: /note= "Norvaline"

(ix) FEATURE:
(A) NAME/KEY: Modified-site
(B) LOCATION: 27
(D) OTHER INFORMATION: /note= "Hydroxyproline"

(ix) FEATURE:
(A) NAME/KEY: Modified-site

-continued (B) LOCATION: 33
(D) OTHER INFORMATION: /note= "Norvaline"

(ix) FEATURE:
 (A) NAME/KEY: Modified-site
 (B) LOCATION: 39
 (D) OTHER INFORMATION: /note= "Norleucine"

(ix) FEATURE:
 (A) NAME/KEY: Modified-site
 (B) LOCATION: 46
 (D) OTHER INFORMATION: /note= "Norleucine"

(ix) FEATURE:
 (A) NAME/KEY: Modified-site
 (B) LOCATION: 51
 (D) OTHER INFORMATION: /note= "T0.90;P0.10"

(ix) FEATURE:
 (A) NAME/KEY: Modified-site
 (B) LOCATION: 60
 (D) OTHER INFORMATION: /note= "Hydroxyproline"

(xi) SEQUENCE DESCRIPTION: SEQ ID NO:25:

Lys Lys Lys Ser Thr Ile Pro Lys Pro Gln Xaa Lys Thr Lys Arg Asn
1               5                   10                  15

Thr Asn Lys Arg Pro Gln Asp Xaa Lys Phe Xaa Gly Gly Gly Gln Ile
            20                  25                  30

Xaa Gly Gly Val Tyr Leu Xaa Pro Arg Arg Gly Pro Arg Xaa Gly Leu
        35                  40                  45

Arg Ala Thr Arg Lys Thr Thr Glu Arg Ser Gln Xaa Arg Gly Arg Arg
    50                  55                  60

(2) INFORMATION FOR SEQ ID NO:26:

(i) SEQUENCE CHARACTERISTICS:
  (A) LENGTH: 64 amino acids
  (B) TYPE: amino acid
  (D) TOPOLOGY: linear (ii) MOLECULE TYPE: peptide (ix) FEATURE:
  (A) NAME/KEY: Modified-site
  (B) LOCATION: 7
  (D) OTHER INFORMATION: /note= "P0.90;G0.10"

(ix) FEATURE:
  (A) NAME/KEY: Modified-site
  (B) LOCATION: 11
  (D) OTHER INFORMATION: /note= "Ornithine"

(ix) FEATURE:
  (A) NAME/KEY: Modified-site
  (B) LOCATION: 13
  (D) OTHER INFORMATION: /note= "T0.70;N0.30"

(ix) FEATURE:
  (A) NAME/KEY: Modified-site
  (B) LOCATION: 24
  (D) OTHER INFORMATION: /note= "Norvaline"

(ix) FEATURE:
  (A) NAME/KEY: Modified-site
  (B) LOCATION: 33
  (D) OTHER INFORMATION: /note= "Norvaline"

(ix) FEATURE:
  (A) NAME/KEY: Modified-site
  (B) LOCATION: 39
  (D) OTHER INFORMATION: /note= "Norleucine"

(ix) FEATURE:
  (A) NAME/KEY: Modified-site
  (B) LOCATION: 46

( D ) OTHER INFORMATION: /note= "Norleucine"

( i x ) FEATURE:
    ( A ) NAME/KEY: Modified-site
    ( B ) LOCATION: 51
    ( D ) OTHER INFORMATION: /note= "T0.90;P0.10"

( i x ) FEATURE:
    ( A ) NAME/KEY: Modified-site
    ( B ) LOCATION: 53
    ( D ) OTHER INFORMATION: /note= "Ornithine"

( i x ) FEATURE:
    ( A ) NAME/KEY: Modified-site
    ( B ) LOCATION: 55
    ( D ) OTHER INFORMATION: /note= "T0.25;A0.25;E0.25;K0.25"

( i x ) FEATURE:
    ( A ) NAME/KEY: Modified-site
    ( B ) LOCATION: 60
    ( D ) OTHER INFORMATION: /note= "Hydroxyproline"

( x i ) SEQUENCE DESCRIPTION: SEQ ID NO:26:

```
Lys Lys Lys Ser Thr Ile Pro Lys Pro Gln Xaa Lys Thr Lys Arg Asn
  1               5                  10                  15

Thr Asn Lys Arg Pro Gln Asp Xaa Lys Phe Pro Gly Gly Gly Asn Ile
             20                  25                  30

Xaa Gly Gly Val Tyr Leu Xaa Pro Arg Arg Gly Pro Arg Xaa Gly Val
         35                  40                  45

Arg Ala Thr Arg Xaa Thr Thr Glu Arg Ser Gln Xaa Arg Gly Arg Arg
     50                  55                  60
```

( 2 ) INFORMATION FOR SEQ ID NO:27:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:27:

```
Ile Ile Pro Asp Arg Glu Val Leu Tyr Met
  1               5                  10
```

( 2 ) INFORMATION FOR SEQ ID NO:28:

( i ) SEQUENCE CHARACTERISTICS:
        ( A ) LENGTH: 50 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 15
        ( D ) OTHER INFORMATION: /note= "Norvaline"

( i x ) FEATURE:
        ( A ) NAME/KEY: Modified-site
        ( B ) LOCATION: 33
        ( D ) OTHER INFORMATION: /note= "Norleucine"

( x i ) SEQUENCE DESCRIPTION: SEQ ID NO:28:

```
Lys Lys Lys Ser Gly Lys Pro Thr Ile Ile Pro Asp Arg Glu Xaa Leu
  1               5                  10                  15

Tyr Arg Glu Phe Asp Asp Met Glu Asp Cys Ser Gln His Leu Pro Tyr
             20                  25                  30

Xaa Asp Gln Gly Met Met Leu Ala Glu Asn Phe Lys Gln Lys Ala Val
```

Gly Leu
50

(2) INFORMATION FOR SEQ ID NO:29:

(i) SEQUENCE CHARACTERISTICS:
        (A) LENGTH: 59 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /note= "S0.80;N0.20"

(ix) FEATURE:
        (A) NAME/KEY: Modified-site
        (B) LOCATION: 5
        (D) OTHER INFORMATION: /note= "G0.80;D0.10;Q0.10"

(ix) FEATURE:
        (A) NAME/KEY: Modified-site
        (B) LOCATION: 6
        (D) OTHER INFORMATION: /note= "K0.60;R0.40"

(ix) FEATURE:
        (A) NAME/KEY: Modified-site
        (B) LOCATION: 7
        (D) OTHER INFORMATION: /note= "P0.80;V0.10;A0.10"

(ix) FEATURE:
        (A) NAME/KEY: Modified-site
        (B) LOCATION: 9
        (D) OTHER INFORMATION: /note= "I0.60;V0.40"

(ix) FEATURE:
        (A) NAME/KEY: Modified-site
        (B) LOCATION: 10
        (D) OTHER INFORMATION: /note= "I0.60;V0.20;A0.20"

(ix) FEATURE:
        (A) NAME/KEY: Modified-site
        (B) LOCATION: 13
        (D) OTHER INFORMATION: /note= "R0.80;K0.20"

(ix) FEATURE:
        (A) NAME/KEY: Modified-site
        (B) LOCATION: 15
        (D) OTHER INFORMATION: /note= "Norvaline"

(ix) FEATURE:
        (A) NAME/KEY: Modified-site
        (B) LOCATION: 18
        (D) OTHER INFORMATION: /note= "R0.30;Q0.50;E0.20"

(ix) FEATURE:
        (A) NAME/KEY: Modified-site
        (B) LOCATION: 19
        (D) OTHER INFORMATION: /note= "E0.80;A0.20"

(ix) FEATURE:
        (A) NAME/KEY: Modified-site
        (B) LOCATION: 27
        (D) OTHER INFORMATION: /note= "S0.40;A0.60"

(ix) FEATURE:
        (A) NAME/KEY: Modified-site
        (B) LOCATION: 28
        (D) OTHER INFORMATION: /note= "Q0.40;S0.60"

(ix) FEATURE:
        (A) NAME/KEY: Modified-site
        (B) LOCATION: 29
        (D) OTHER INFORMATION: /note= "H0.80;K0.10;R0.10"

(ix) FEATURE:
    (A) NAME/KEY: Modified-site
    (B) LOCATION: 30
    (D) OTHER INFORMATION: /note= "L0.80;A0.20"

(ix) FEATURE:
    (A) NAME/KEY: Modified-site
    (B) LOCATION: 31
    (D) OTHER INFORMATION: /note= "P0.80;A0.20"

(ix) FEATURE:
    (A) NAME/KEY: Modified-site
    (B) LOCATION: 32
    (D) OTHER INFORMATION: /note= "Y0.80;L0.20"

(ix) FEATURE:
    (A) NAME/KEY: Modified-site
    (B) LOCATION: 33
    (D) OTHER INFORMATION: /note= "Norleucine"

(ix) FEATURE:
    (A) NAME/KEY: Modified-site
    (B) LOCATION: 35
    (D) OTHER INFORMATION: /note= "Q0.80;E0.20"

(ix) FEATURE:
    (A) NAME/KEY: Modified-site
    (B) LOCATION: 37
    (D) OTHER INFORMATION: /note= "M0.80;Q0.20"

(ix) FEATURE:
    (A) NAME/KEY: Modified-site
    (B) LOCATION: 38
    (D) OTHER INFORMATION: /note= "M0.40;Q0.40;R0.20"

(ix) FEATURE:
    (A) NAME/KEY: Modified-site
    (B) LOCATION: 39
    (D) OTHER INFORMATION: /note= "L0.80;M0.10;I0.10"

(ix) FEATURE:
    (A) NAME/KEY: Modified-site
    (B) LOCATION: 43
    (D) OTHER INFORMATION: /note= "F0.80;L0.20"

(ix) FEATURE:
    (A) NAME/KEY: Modified-site
    (B) LOCATION: 45
    (D) OTHER INFORMATION: /note= "Q0.80;S0.20"

(ix) FEATURE:
    (A) NAME/KEY: Modified-site
    (B) LOCATION: 47
    (D) OTHER INFORMATION: /note= "A0.80;I0.20"

(xi) SEQUENCE DESCRIPTION: SEQ ID NO:29:

```
Lys Lys Lys Ser Gly Lys Pro Thr Ile Ile Pro Asp Arg Glu Xaa Leu
 1               5                   10                  15
Tyr Arg Glu Phe Asp Asp Met Glu Asp Cys Ser Gln His Leu Pro Tyr
                20              25                  30
Xaa Asp Gln Gly Met Met Leu Ala Glu Asn Phe Lys Gln Lys Ala Val
            35              40                  45
Gly Leu Val Lys Phe Pro Gly Gly Gly Asn Ile
        50              55
```

(2) INFORMATION FOR SEQ ID NO:30:

(i) SEQUENCE CHARACTERISTICS:
        (A) LENGTH: 59 amino acids
        (B) TYPE: amino acid
        (D) TOPOLOGY: linear (ii) MOLECULE TYPE: peptide (ix) FEATURE:

( A ) NAME/KEY: Modified-site
                    ( B ) LOCATION: 4
                    ( D ) OTHER INFORMATION: /note= "S0.80;N0.20"

( i x ) FEATURE:
                    ( A ) NAME/KEY: Modified-site
                    ( B ) LOCATION: 5
                    ( D ) OTHER INFORMATION: /note= "G0.80;D0.10;Q0.10"

( i x ) FEATURE:
                    ( A ) NAME/KEY: Modified-site
                    ( B ) LOCATION: 6
                    ( D ) OTHER INFORMATION: /note= "K0.60;R0.40"

( i x ) FEATURE:
                    ( A ) NAME/KEY: Modified-site
                    ( B ) LOCATION: 7
                    ( D ) OTHER INFORMATION: /note= "P0.80;V0.10;A0.10"

( i x ) FEATURE:
                    ( A ) NAME/KEY: Modified-site
                    ( B ) LOCATION: 9
                    ( D ) OTHER INFORMATION: /note= "I0.60;V0.40"

( i x ) FEATURE:
                    ( A ) NAME/KEY: Modified-site
                    ( B ) LOCATION: 10
                    ( D ) OTHER INFORMATION: /note= "I0.60;V0.20;A0.20"

( i x ) FEATURE:
                    ( A ) NAME/KEY: Modified-site
                    ( B ) LOCATION: 13
                    ( D ) OTHER INFORMATION: /note= "R0.80;K0.20"

( i x ) FEATURE:
                    ( A ) NAME/KEY: Modified-site
                    ( B ) LOCATION: 15
                    ( D ) OTHER INFORMATION: /note= "Norvaline"

( i x ) FEATURE:
                    ( A ) NAME/KEY: Modified-site
                    ( B ) LOCATION: 18
                    ( D ) OTHER INFORMATION: /note= "R0.30;Q0.50;E0.20"

( i x ) FEATURE:
                    ( A ) NAME/KEY: Modified-site
                    ( B ) LOCATION: 19
                    ( D ) OTHER INFORMATION: /note= "E0.80;A0.20"

( i x ) FEATURE:
                    ( A ) NAME/KEY: Modified-site
                    ( B ) LOCATION: 27
                    ( D ) OTHER INFORMATION: /note= "S0.40;A0.60"

( i x ) FEATURE:
                    ( A ) NAME/KEY: Modified-site
                    ( B ) LOCATION: 28
                    ( D ) OTHER INFORMATION: /note= "Q0.40;S0.60"

( i x ) FEATURE:
                    ( A ) NAME/KEY: Modified-site
                    ( B ) LOCATION: 29
                    ( D ) OTHER INFORMATION: /note= "H0.80;K0.10;R0.10"

( i x ) FEATURE:
                    ( A ) NAME/KEY: Modified-site
                    ( B ) LOCATION: 30
                    ( D ) OTHER INFORMATION: /note= "L0.80;A0.20"

( i x ) FEATURE:
                    ( A ) NAME/KEY: Modified-site
                    ( B ) LOCATION: 31
                    ( D ) OTHER INFORMATION: /note= "P0.80;A0.20"

( i x ) FEATURE:
                    ( A ) NAME/KEY: Modified-site
                    ( B ) LOCATION: 32
                    ( D ) OTHER INFORMATION: /note= "Y0.80;L0.20"

( i x ) FEATURE:

(A) NAME/KEY: Modified-site
(B) LOCATION: 33
(D) OTHER INFORMATION: /note= "Norvaline"

(ix) FEATURE:
(A) NAME/KEY: Modified-site
(B) LOCATION: 35
(D) OTHER INFORMATION: /note= "Q0.80;E0.20"

(ix) FEATURE:
(A) NAME/KEY: Modified-site
(B) LOCATION: 37
(D) OTHER INFORMATION: /note= "M0.80;Q0.20"

(ix) FEATURE:
(A) NAME/KEY: Modified-site
(B) LOCATION: 38
(D) OTHER INFORMATION: /note= "M0.40;Q0.40;R0.20"

(ix) FEATURE:
(A) NAME/KEY: Modified-site
(B) LOCATION: 39
(D) OTHER INFORMATION: /note= "L0.80;M0.10;I0.10"

(ix) FEATURE:
(A) NAME/KEY: Modified-site
(B) LOCATION: 43
(D) OTHER INFORMATION: /note= "F0.80;L0.20"

(ix) FEATURE:
(A) NAME/KEY: Modified-site
(B) LOCATION: 45
(D) OTHER INFORMATION: /note= "Q0.80;S0.20"

(ix) FEATURE:
(A) NAME/KEY: Modified-site
(B) LOCATION: 47
(D) OTHER INFORMATION: /note= "A0.80;I0.20"

(ix) FEATURE:
(A) NAME/KEY: Modified-site
(B) LOCATION: 48
(D) OTHER INFORMATION: /note= "Norvaline"

(xi) SEQUENCE DESCRIPTION: SEQ ID NO:30:

```
Lys  Lys  Lys  Ser  Gly  Lys  Pro  Thr  Ile  Ile  Pro  Asp  Arg  Glu  Xaa  Leu
1                 5                            10                           15

Tyr  Arg  Glu  Phe  Asp  Asp  Met  Glu  Asp  Cys  Ser  Gln  His  Leu  Pro  Tyr
                20                       25                      30

Xaa  Asp  Gln  Gly  Met  Met  Leu  Ala  Glu  Asn  Phe  Lys  Gln  Lys  Ala  Xaa
           35                      40                           45

Gly  Leu  Val  Lys  Phe  Pro  Gly  Gly  Gly  Asn  Ile
          50                 55
```

(2) INFORMATION FOR SEQ ID NO:31:

(i) SEQUENCE CHARACTERISTICS:
(A) LENGTH: 41 amino acids
(B) TYPE: amino acid
(D) TOPOLOGY: linear (ii) MOLECULE TYPE: peptide (ix) FEATURE:
(A) NAME/KEY: Modified-site
(B) LOCATION: 5
(D) OTHER INFORMATION: /note= "P0.80;L0.10;V0.10"

(ix) FEATURE:
(A) NAME/KEY: Modified-site
(B) LOCATION: 7
(D) OTHER INFORMATION: /note= "Norvaline"

(ix) FEATURE:
(A) NAME/KEY: Modified-site (B) LOCATION: 9
(D) OTHER INFORMATION: /note= "T0.50;S0.40;P0.10"

( i x ) FEATURE:
(A) NAME/KEY: Modified-site
(B) LOCATION: 12
(D) OTHER INFORMATION: /note= "K0.40;D0.40;R0.20"

( i x ) FEATURE:
(A) NAME/KEY: Modified-site
(B) LOCATION: 16
(D) OTHER INFORMATION: /note= "E0.50;V0.40;Q0.10"

( i x ) FEATURE:
(A) NAME/KEY: Modified-site
(B) LOCATION: 18
(D) OTHER INFORMATION: /note= "P0.90;A0.10"

( i x ) FEATURE:
(A) NAME/KEY: Modified-site
(B) LOCATION: 19
(D) OTHER INFORMATION: /note= "V0.80;T0.20"

( i x ) FEATURE:
(A) NAME/KEY: Modified-site
(B) LOCATION: 20
(D) OTHER INFORMATION: /note= "Norvaline"

( i x ) FEATURE:
(A) NAME/KEY: Modified-site
(B) LOCATION: 21
(D) OTHER INFORMATION: /note= "H0.80;L0.10;A0.10"

( i x ) FEATURE:
(A) NAME/KEY: Modified-site
(B) LOCATION: 24
(D) OTHER INFORMATION: /note= "P0.80;A0.20"

( i x ) FEATURE:
(A) NAME/KEY: Modified-site
(B) LOCATION: 27
(D) OTHER INFORMATION: /note= "P0.90;S0.10"

( i x ) FEATURE:
(A) NAME/KEY: Modified-site
(B) LOCATION: 28
(D) OTHER INFORMATION: /note= "Hydroxyproline"

( i x ) FEATURE:
(A) NAME/KEY: Modified-site
(B) LOCATION: 29
(D) OTHER INFORMATION: /note= "K0.80;P0.10;R0.10"

( i x ) FEATURE:
(A) NAME/KEY: Modified-site
(B) LOCATION: 30
(D) OTHER INFORMATION: /note= "S0.40;A0.40;K0.10;Q0.10"

( i x ) FEATURE:
(A) NAME/KEY: Modified-site
(B) LOCATION: 31
(D) OTHER INFORMATION: /note= "P0.80;T0.20"

( i x ) FEATURE:
(A) NAME/KEY: Modified-site
(B) LOCATION: 33
(D) OTHER INFORMATION: /note= "V0.50;I0.40;T0.10"

( i x ) FEATURE:
(A) NAME/KEY: Modified-site
(B) LOCATION: 34
(D) OTHER INFORMATION: /note= "Hydroxyproline"

( i x ) FEATURE:
(A) NAME/KEY: Modified-site
(B) LOCATION: 38
(D) OTHER INFORMATION: /note= "K0.40;R0.60"

( i x ) FEATURE:
(A) NAME/KEY: Modified-site (B) LOCATION: 39
(D) OTHER INFORMATION: /note= "K0.70;R0.30"

(ix) FEATURE:
(A) NAME/KEY: Modified-site
(B) LOCATION: 41
(D) OTHER INFORMATION: /note= "T0.90;A0.10"

(xi) SEQUENCE DESCRIPTION: SEQ ID NO:31:

| Asp | Tyr | Asn | Pro | Pro | Leu | Xaa | Glu | Thr | Trp | Lys | Lys | Pro | Glu | Tyr | Glu |
|---|---|---|---|---|---|---|---|---|---|---|---|---|---|---|---|
| 1 | | | | 5 | | | | | 10 | | | | | 15 | |
| Pro | Pro | Val | Xaa | His | Gly | Cys | Pro | Leu | Pro | Pro | Xaa | Lys | Ser | Pro | Pro |
| | | | 20 | | | | | 25 | | | | | 30 | | |
| Val | Xaa | Pro | Pro | Arg | Lys | Lys | Arg | Thr | | | | | | | |
| | | 35 | | | | | | 40 | | | | | | | |

(2) INFORMATION FOR SEQ ID NO:32:

(i) SEQUENCE CHARACTERISTICS:
(A) LENGTH: 42 amino acids
(B) TYPE: amino acid
(D) TOPOLOGY: linear (ii) MOLECULE TYPE: peptide (ix) FEATURE:
(A) NAME/KEY: Modified-site
(B) LOCATION: 6
(D) OTHER INFORMATION: /note= "P0.80;L0.10;V0.10"

(ix) FEATURE:
(A) NAME/KEY: Modified-site
(B) LOCATION: 8
(D) OTHER INFORMATION: /note= "Norvaline"

(ix) FEATURE:
(A) NAME/KEY: Modified-site
(B) LOCATION: 10
(D) OTHER INFORMATION: /note= "T0.50;S0.40;P0.10"

(ix) FEATURE:
(A) NAME/KEY: Modified-site
(B) LOCATION: 13
(D) OTHER INFORMATION: /note= "K0.40;D0.40;R0.20"

(ix) FEATURE:
(A) NAME/KEY: Modified-site
(B) LOCATION: 17
(D) OTHER INFORMATION: /note= "E0.50;V0.40;Q0.10"

(ix) FEATURE:
(A) NAME/KEY: Modified-site
(B) LOCATION: 19
(D) OTHER INFORMATION: /note= "P0.90;A0.10"

(ix) FEATURE:
(A) NAME/KEY: Modified-site
(B) LOCATION: 20
(D) OTHER INFORMATION: /note= "V0.80;T0.20"

(ix) FEATURE:
(A) NAME/KEY: Modified-site
(B) LOCATION: 21
(D) OTHER INFORMATION: /note= "Norvaline"

(ix) FEATURE:
(A) NAME/KEY: Modified-site
(B) LOCATION: 22
(D) OTHER INFORMATION: /note= "H0.80;L0.10;A0.10"

(ix) FEATURE:
(A) NAME/KEY: Modified-site
(B) LOCATION: 25
(D) OTHER INFORMATION: /note= "P0.80;A0.20"

(ix) FEATURE:

(A) NAME/KEY: Modified-site
(B) LOCATION: 28
(D) OTHER INFORMATION: /note= "P0.90;S0.10"

(ix) FEATURE:
(A) NAME/KEY: Modified-site
(B) LOCATION: 29
(D) OTHER INFORMATION: /note= "Hydroxyproline"

(ix) FEATURE:
(A) NAME/KEY: Modified-site
(B) LOCATION: 30
(D) OTHER INFORMATION: /note= "K0.80;P0.10;R0.10"

(ix) FEATURE:
(A) NAME/KEY: Modified-site
(B) LOCATION: 31
(D) OTHER INFORMATION: /note= "S0.40;A0.40;K0.10;Q0.10"

(ix) FEATURE:
(A) NAME/KEY: Modified-site
(B) LOCATION: 32
(D) OTHER INFORMATION: /note= "P0.80;T0.20"

(ix) FEATURE:
(A) NAME/KEY: Modified-site
(B) LOCATION: 34
(D) OTHER INFORMATION: /note= "V0.50;I0.40;T0.10"

(ix) FEATURE:
(A) NAME/KEY: Modified-site
(B) LOCATION: 35
(D) OTHER INFORMATION: /note= "Hydroxyproline"

(ix) FEATURE:
(A) NAME/KEY: Modified-site
(B) LOCATION: 39
(D) OTHER INFORMATION: /note= "K0.40;R0.60"

(ix) FEATURE:
(A) NAME/KEY: Modified-site
(B) LOCATION: 40
(D) OTHER INFORMATION: /note= "K0.70;R0.30"

(ix) FEATURE:
(A) NAME/KEY: Modified-site
(B) LOCATION: 42
(D) OTHER INFORMATION: /note= "T0.90;A0.10"

(xi) SEQUENCE DESCRIPTION: SEQ ID NO:32:

```
Pro Asp Tyr Asn Pro Pro Leu Xaa Glu Thr Trp Lys Lys Pro Glu Tyr
 1               5                  10                 15
Glu Pro Pro Val Xaa His Gly Cys Pro Leu Pro Pro Xaa Lys Ser Pro
             20              25              30
Pro Val Xaa Pro Pro Arg Lys Lys Arg Thr
         35              40
```

(2) INFORMATION FOR SEQ ID NO:33:

(i) SEQUENCE CHARACTERISTICS:
(A) LENGTH: 44 amino acids
(B) TYPE: amino acid
(D) TOPOLOGY: linear (ii) MOLECULE TYPE: peptide (ix) FEATURE:
(A) NAME/KEY: Modified-site
(B) LOCATION: 8
(D) OTHER INFORMATION: /note= "P0.80;L0.10;V0.10"

(ix) FEATURE:
(A) NAME/KEY: Modified-site
(B) LOCATION: 10
(D) OTHER INFORMATION: /note= "Norvaline"

-continued

```
( i x ) FEATURE:
        ( A ) NAME/KEY: Modified-site
        ( B ) LOCATION: 12
        ( D ) OTHER INFORMATION: /note= "T0.50;S0.40;P0.10"

( i x ) FEATURE:
        ( A ) NAME/KEY: Modified-site
        ( B ) LOCATION: 15
        ( D ) OTHER INFORMATION: /note= "K0.40;D0.40;R0.20"

( i x ) FEATURE:
        ( A ) NAME/KEY: Modified-site
        ( B ) LOCATION: 19
        ( D ) OTHER INFORMATION: /note= "E0.50;V0.40;Q0.10"

( i x ) FEATURE:
        ( A ) NAME/KEY: Modified-site
        ( B ) LOCATION: 21
        ( D ) OTHER INFORMATION: /note= "P0.90;A0.10"

( i x ) FEATURE:
        ( A ) NAME/KEY: Modified-site
        ( B ) LOCATION: 22
        ( D ) OTHER INFORMATION: /note= "V0.80;T0.20"

( i x ) FEATURE:
        ( A ) NAME/KEY: Modified-site
        ( B ) LOCATION: 23
        ( D ) OTHER INFORMATION: /note= "Norvaline"

( i x ) FEATURE:
        ( A ) NAME/KEY: Modified-site
        ( B ) LOCATION: 24
        ( D ) OTHER INFORMATION: /note= "H0.80;L0.10;A0.10"

( i x ) FEATURE:
        ( A ) NAME/KEY: Modified-site
        ( B ) LOCATION: 27
        ( D ) OTHER INFORMATION: /note= "P0.80;A0.20"

( i x ) FEATURE:
        ( A ) NAME/KEY: Modified-site
        ( B ) LOCATION: 30
        ( D ) OTHER INFORMATION: /note= "P0.90;S0.10"

( i x ) FEATURE:
        ( A ) NAME/KEY: Modified-site
        ( B ) LOCATION: 31
        ( D ) OTHER INFORMATION: /note= "Hydroxyproline"

( i x ) FEATURE:
        ( A ) NAME/KEY: Modified-site
        ( B ) LOCATION: 32
        ( D ) OTHER INFORMATION: /note= "K0.80;P0.10;R0.10"

( i x ) FEATURE:
        ( A ) NAME/KEY: Modified-site
        ( B ) LOCATION: 33
        ( D ) OTHER INFORMATION: /note= "S0.40;A0.40;K0.10;Q0.10"

( i x ) FEATURE:
        ( A ) NAME/KEY: Modified-site
        ( B ) LOCATION: 34
        ( D ) OTHER INFORMATION: /note= "P0.80;T0.20"

( i x ) FEATURE:
        ( A ) NAME/KEY: Modified-site
        ( B ) LOCATION: 36
        ( D ) OTHER INFORMATION: /note= "V0.50;I0.40;T0.10"

( i x ) FEATURE:
        ( A ) NAME/KEY: Modified-site
        ( B ) LOCATION: 37
        ( D ) OTHER INFORMATION: /note= "Hydroxyproline"

( i x ) FEATURE:
        ( A ) NAME/KEY: Modified-site
        ( B ) LOCATION: 41
        ( D ) OTHER INFORMATION: /note= "K0.40;R0.60"
```

( i x ) FEATURE:
  ( A ) NAME/KEY: Modified-site
  ( B ) LOCATION: 42
  ( D ) OTHER INFORMATION: /note= "K0.70;R0.30"

( i x ) FEATURE:
  ( A ) NAME/KEY: Modified-site
  ( B ) LOCATION: 44
  ( D ) OTHER INFORMATION: /note= "T0.90;A0.10"

( i x ) FEATURE:
  ( A ) NAME/KEY: Modified-site
  ( B ) LOCATION: 2
  ( D ) OTHER INFORMATION: /note= "Ornithine"

( x i ) SEQUENCE DESCRIPTION: SEQ ID NO:33:

```
Ala  Xaa  Pro  Asp  Tyr  Asn  Pro  Pro  Leu  Xaa  Glu  Thr  Trp  Lys  Lys  Pro
1                  5                        10                            15

Glu  Tyr  Glu  Pro  Pro  Val  Xaa  His  Gly  Cys  Pro  Leu  Pro  Pro  Xaa  Lys
               20                  25                            30

Ser  Pro  Pro  Val  Xaa  Pro  Pro  Arg  Lys  Lys  Arg  Thr
          35                  40
```

( 2 ) INFORMATION FOR SEQ ID NO:34:

( i ) SEQUENCE CHARACTERISTICS:
    ( A ) LENGTH: 37 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 3
    ( D ) OTHER INFORMATION: /note= "Norvaline"

( i x ) FEATURE:
    ( A ) NAME/KEY: Modified-site
    ( B ) LOCATION: 16
    ( D ) OTHER INFORMATION: /note= "Norvaline"

( i x ) FEATURE:
    ( A ) NAME/KEY: Modified-site
    ( B ) LOCATION: 24
    ( D ) OTHER INFORMATION: /note= "Hydroxyproline"

( i x ) FEATURE:
    ( A ) NAME/KEY: Modified-site
    ( B ) LOCATION: 32
    ( D ) OTHER INFORMATION: /note= "Hydroxyproline"

( x i ) SEQUENCE DESCRIPTION: SEQ ID NO:34:

```
Pro  Leu  Xaa  Glu  Thr  Trp  Lys  Lys  Pro  Glu  Tyr  Glu  Pro  Pro  Val  Xaa
1                  5                        10                            15

His  Gly  Cys  Pro  Leu  Pro  Pro  Xaa  Lys  Ser  Pro  Pro  Val  Pro  Pro  Xaa
               20                  25                            30

Arg  Lys  Lys  Arg  Thr
          35
```

( 2 ) INFORMATION FOR SEQ ID NO:35:

( i ) SEQUENCE CHARACTERISTICS:
    ( A ) LENGTH: 40 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:35:

```
Lys  Gln  Lys  Ala  Leu  Gly  Leu  Leu  Gln  Thr  Ala  Ser  Arg  Gln  Ala  Glu
```

```
                 1               5                         10                        15
            Val Ile Ala Pro Ala Val Gln Thr Asn Trp Gln Lys Leu Glu Thr Phe
                         20                      25                    30
            Trp Ala Lys His Met Trp Asn Phe
                         35                  40
```

( 2 ) INFORMATION FOR SEQ ID NO:36:

( i ) SEQUENCE CHARACTERISTICS:
        ( A ) LENGTH: 55 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:36:

```
            Lys Ala Thr Cys Thr Ala Asn His Asp Ser Pro Asp Ala Glu Leu Ile
            1               5                         10                        15
            Glu Ala Asn Leu Leu Trp Arg Gln Glu Met Gly Gly Asn Ile Thr Arg
                         20                      25                    30
            Val Glu Ser Glu Asn Lys Val Val Ile Leu Asp Ser Phe Asp Pro Leu
                         35                      40                    45
            Val Ala Glu Glu Asp Glu Arg
                         50                  55
```

( 2 ) INFORMATION FOR SEQ ID NO:37:

( i ) SEQUENCE CHARACTERISTICS:
        ( A ) LENGTH: 55 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 11
        ( D ) OTHER INFORMATION: /note= "Ornithine"

( i x ) FEATURE:
        ( A ) NAME/KEY: Modified-site
        ( B ) LOCATION: 19
        ( D ) OTHER INFORMATION: /note= "Ornithine"

( i x ) FEATURE:
        ( A ) NAME/KEY: Modified-site
        ( B ) LOCATION: 27
        ( D ) OTHER INFORMATION: /note= "Hydroxyproline"

( i x ) FEATURE:
        ( A ) NAME/KEY: Modified-site
        ( B ) LOCATION: 32
        ( D ) OTHER INFORMATION: /note= "Norvaline"

( i x ) FEATURE:
        ( A ) NAME/KEY: Modified-site
        ( B ) LOCATION: 40
        ( D ) OTHER INFORMATION: /note= "Hydroxyproline"

( i x ) FEATURE:
        ( A ) NAME/KEY: Modified-site
        ( B ) LOCATION: 46
        ( D ) OTHER INFORMATION: /note= "Norleucine"

( x i ) SEQUENCE DESCRIPTION: SEQ ID NO:37:

```
            Lys Lys Lys Ser Thr Ile Pro Lys Pro Xaa Lys Thr Lys Arg Asn
            1               5                         10                        15
            Thr Asn Xaa Arg Pro Gln Asp Val Lys Phe Xaa Gly Gly Gly Gln Xaa
                         20                      25                    30
```

```
            Val  Gly  Gly  Val  Tyr  Leu  Leu  Xaa  Arg  Arg  Gly  Pro  Arg  Xaa  Gly  Xaa
                      35                            40                       45

Arg  Ala  Thr  Arg  Lys  Thr  Ser
                 50                       55
```

(2) INFORMATION FOR SEQ ID NO:38:

(i) SEQUENCE CHARACTERISTICS:
      (A) LENGTH: 46 amino acids
      (B) TYPE: amino acid
      (D) TOPOLOGY: linear (ii) MOLECULE TYPE: peptide (ix) FEATURE:
      (A) NAME/KEY: Modified-site
      (B) LOCATION: 18
      (D) OTHER INFORMATION: /note= "Hydroxyproline"

(ix) FEATURE:
      (A) NAME/KEY: Modified-site
      (B) LOCATION: 23
      (D) OTHER INFORMATION: /note= "Norvaline"

(ix) FEATURE:
      (A) NAME/KEY: Modified-site
      (B) LOCATION: 31
      (D) OTHER INFORMATION: /note= "Hydroxyproline"

(ix) FEATURE:
      (A) NAME/KEY: Modified-site
      (B) LOCATION: 37
      (D) OTHER INFORMATION: /note= "Norleucine"

(ix) FEATURE:
      (A) NAME/KEY: Modified-site
      (B) LOCATION: 39
      (D) OTHER INFORMATION: /note= "Norvaline"

(xi) SEQUENCE DESCRIPTION: SEQ ID NO:38:

```
            Lys  Lys  Lys  Thr  Lys  Arg  Asn  Thr  Asn  Lys  Arg  Pro  Gln  Asp  Val  Lys
            1                   5                        10                       15

Phe  Xaa  Gly  Gly  Gly  Gln  Xaa  Val  Gly  Gly  Val  Tyr  Leu  Leu  Xaa  Arg
                      20                       25                            30

Arg  Gly  Pro  Arg  Xaa  Gly  Xaa  Arg  Ala  Thr  Arg  Lys  Thr  Ser
                      35                       40                       45
```

(2) INFORMATION FOR SEQ ID NO:39:

(i) SEQUENCE CHARACTERISTICS:
      (A) LENGTH: 50 amino acids
      (B) TYPE: amino acid
      (D) TOPOLOGY: linear (ii) MOLECULE TYPE: peptide (xi) SEQUENCE DESCRIPTION: SEQ ID NO:39:

```
            Lys  Lys  Lys  Ser  Gly  Lys  Pro  Thr  Ile  Ile  Pro  Asp  Arg  Glu  Xaa  Leu
            1                   5                        10                       15

Tyr  Arg  Glu  Phe  Asp  Glu  Met  Glu  Asp  Cys  Ser  Gln  His  Leu  Pro  Tyr
                      20                       25                            30

Ile  Asp  Gln  Gly  Met  Met  Leu  Ala  Glu  Asn  Phe  Lys  Gln  Lys  Ala  Val
                      35                       40                       45

Gly  Leu
```

(2) INFORMATION FOR SEQ ID NO:40:

(i) SEQUENCE CHARACTERISTICS:
      (A) LENGTH: 50 amino acids (B) TYPE: amino acid
(D) TOPOLOGY: linear (ii) MOLECULE TYPE: peptide (ix) FEATURE:
(A) NAME/KEY: Modified-site
(B) LOCATION: 15
(D) OTHER INFORMATION: /note= "Norvaline"

(ix) FEATURE:
(A) NAME/KEY: Modified-site
(B) LOCATION: 30
(D) OTHER INFORMATION: /note= "Norvaline"

(xi) SEQUENCE DESCRIPTION: SEQ ID NO:40:

```
Lys Lys Lys Ser Gly Lys Pro Thr Ile Ile Pro Asp Arg Glu Xaa Leu
 1               5                  10                      15

Tyr Arg Glu Phe Asp Glu Met Glu Asp Cys Ser Gln His Xaa Pro Tyr
             20                  25                  30

Ile Asp Gln Gly Met Met Leu Ala Glu Asn Phe Lys Gln Lys Ala Val
             35                  40                  45

Gly Leu
     50
```

(2) INFORMATION FOR SEQ ID NO:41:

(i) SEQUENCE CHARACTERISTICS:
(A) LENGTH: 50 amino acids
(B) TYPE: amino acid
(D) TOPOLOGY: linear (ii) MOLECULE TYPE: peptide (ix) FEATURE:
(A) NAME/KEY: Modified-site
(B) LOCATION: 15
(D) OTHER INFORMATION: /note= "Norvaline"

(ix) FEATURE:
(A) NAME/KEY: Modified-site
(B) LOCATION: 18
(D) OTHER INFORMATION: /note= "Ornithine"

(ix) FEATURE:
(A) NAME/KEY: Modified-site
(B) LOCATION: 30
(D) OTHER INFORMATION: /note= "Norvaline"

(xi) SEQUENCE DESCRIPTION: SEQ ID NO:41:

```
Lys Lys Lys Ser Gly Lys Pro Thr Ile Ile Pro Asp Arg Glu Xaa Leu
 1               5                  10                      15

Tyr Xaa Glu Phe Asp Glu Met Glu Asp Cys Ser Gln His Xaa Pro Tyr
             20                  25                  30

Ile Asp Gln Gly Met Met Leu Ala Glu Asn Phe Lys Gln Lys Ala Val
             35                  40                  45

Gly Leu
     50
```

(2) INFORMATION FOR SEQ ID NO:42:

(i) SEQUENCE CHARACTERISTICS:
(A) LENGTH: 50 amino acids
(B) TYPE: amino acid
(D) TOPOLOGY: linear (ii) MOLECULE TYPE: peptide (ix) FEATURE:
(A) NAME/KEY: Modified-site (B) LOCATION: 7
(D) OTHER INFORMATION: /note= "Hydroxyproline"

(ix) FEATURE:
(A) NAME/KEY: Modified-site
(B) LOCATION: 15
(D) OTHER INFORMATION: /note= "Norvaline"

(ix) FEATURE:
(A) NAME/KEY: Modified-site
(B) LOCATION: 18
(D) OTHER INFORMATION: /note= "Ornithine"

(xi) SEQUENCE DESCRIPTION: SEQ ID NO:42:

```
Lys Lys Lys Asn Gln Arg Xaa Ser Ile Ile Pro Asp Arg Glu Xaa Leu
1               5                   10                  15

Tyr Xaa Glu Phe Asp Glu Met Glu Asp Cys Ser Gln His Leu Pro Tyr
            20                  25                  30

Ile Asp Gln Gly Met Met Leu Ala Glu Asn Phe Lys Gln Lys Ala Val
        35                  40                  45

Gly Leu
    50
```

(2) INFORMATION FOR SEQ ID NO:43:

(i) SEQUENCE CHARACTERISTICS:
(A) LENGTH: 50 amino acids
(B) TYPE: amino acid
(D) TOPOLOGY: linear (ii) MOLECULE TYPE: peptide (ix) FEATURE:
(A) NAME/KEY: Modified-site
(B) LOCATION: 7
(D) OTHER INFORMATION: /note= "Hydroxyproline"

(ix) FEATURE:
(A) NAME/KEY: Modified-site
(B) LOCATION: 15
(D) OTHER INFORMATION: /note= "Norvaline"

(ix) FEATURE:
(A) NAME/KEY: Modified-site
(B) LOCATION: 18
(D) OTHER INFORMATION: /note= "Ornithine"

(ix) FEATURE:
(A) NAME/KEY: Modified-site
(B) LOCATION: 30
(D) OTHER INFORMATION: /note= "Norvaline"

(xi) SEQUENCE DESCRIPTION: SEQ ID NO:43:

```
Lys Lys Lys Asn Gln Arg Xaa Ser Ile Ile Pro Asp Arg Glu Xaa Leu
1               5                   10                  15

Tyr Xaa Glu Phe Asp Glu Met Glu Asp Cys Ser Gln His Xaa Pro Tyr
            20                  25                  30

Ile Asp Gln Gly Met Met Leu Ala Glu Asn Phe Lys Gln Lys Ala Val
        35                  40                  45

Gly Leu
    50
```

(2) INFORMATION FOR SEQ ID NO:44:

(i) SEQUENCE CHARACTERISTICS:
(A) LENGTH: 45 amino acids
(B) TYPE: amino acid
(D) TOPOLOGY: linear (ii) MOLECULE TYPE: peptide (ix) FEATURE:
    (A) NAME/KEY: Modified-site
    (B) LOCATION: 10
    (D) OTHER INFORMATION: /note= "Norvaline"

(ix) FEATURE:
    (A) NAME/KEY: Modified-site
    (B) LOCATION: 12
    (D) OTHER INFORMATION: /note= "Ornithine"

(ix) FEATURE:
    (A) NAME/KEY: Modified-site
    (B) LOCATION: 25
    (D) OTHER INFORMATION: /note= "Norvaline"

(xi) SEQUENCE DESCRIPTION: SEQ ID NO:44:

```
Lys Lys Lys Ile Ile Pro Asp Arg Glu Xaa Leu Tyr Xaa Glu Phe Asp
1               5                   10                  15

Glu Met Glu Asp Cys Ser Gln His Xaa Pro Tyr Ile Asp Gln Gly Met
            20                  25                  30

Met Leu Ala Glu Asn Phe Lys Gln Lys Ala Val Gly Leu
            35                  40                  45
```

(2) INFORMATION FOR SEQ ID NO:45:

(i) SEQUENCE CHARACTERISTICS:
        (A) LENGTH: 44 amino acids
        (B) TYPE: amino acid
        (D) TOPOLOGY: linear (ii) MOLECULE TYPE: peptide (ix) FEATURE:
    (A) NAME/KEY: Modified-site
    (B) LOCATION: 2
    (D) OTHER INFORMATION: /note= "Ornithine"

(ix) FEATURE:
    (A) NAME/KEY: Modified-site
    (B) LOCATION: 10
    (D) OTHER INFORMATION: /note= "Norvaline"

(ix) FEATURE:
    (A) NAME/KEY: Modified-site
    (B) LOCATION: 23
    (D) OTHER INFORMATION: /note= "Norvaline"

(ix) FEATURE:
    (A) NAME/KEY: Modified-site
    (B) LOCATION: 31
    (D) OTHER INFORMATION: /note= "Hydroxyproline"

(ix) FEATURE:
    (A) NAME/KEY: Modified-site
    (B) LOCATION: 37
    (D) OTHER INFORMATION: /note= "Hydroxyproline"

(xi) SEQUENCE DESCRIPTION: SEQ ID NO:45:

```
Ala Xaa Pro Asp Tyr Asn Pro Pro Leu Xaa Glu Thr Trp Lys Lys Pro
1               5                   10                  15

Glu Tyr Glu Pro Pro Val Xaa His Gly Cys Pro Leu Pro Pro Xaa Lys
            20                  25                  30

Ser Pro Pro Val Xaa Pro Pro Arg Lys Lys Arg Thr
            35                  40
```

(2) INFORMATION FOR SEQ ID NO:46:

(i) SEQUENCE CHARACTERISTICS:
        (A) LENGTH: 40 amino acids
        (B) TYPE: amino acid
        (D) TOPOLOGY: linear (i i) MOLECULE TYPE: peptide (i x) FEATURE:
    (A) NAME/KEY: Modified-site
    (B) LOCATION: 8
    (D) OTHER INFORMATION: /note= "Norleucine"

(i x) FEATURE:
    (A) NAME/KEY: Modified-site
    (B) LOCATION: 13
    (D) OTHER INFORMATION: /note= "Ornithine"

(i x) FEATURE:
    (A) NAME/KEY: Modified-site
    (B) LOCATION: 20
    (D) OTHER INFORMATION: /note= "Hydroxyproline"

(i x) FEATURE:
    (A) NAME/KEY: Modified-site
    (B) LOCATION: 35
    (D) OTHER INFORMATION: /note= "Ornithine"

(x i) SEQUENCE DESCRIPTION: SEQ ID NO:46:

```
Lys Gln Lys Ala Leu Gly Leu Xaa Gln Thr Ala Ser Xaa Gln Ala Glu
 1               5                   10                  15

Val Ile Ala Xaa Ala Val Gln Thr Asn Trp Gln Arg Leu Glu Thr Phe
              20                  25                  30

Trp Ala Xaa His Met Trp Asn Phe
              35              40
```

(2) INFORMATION FOR SEQ ID NO:47:

(i) SEQUENCE CHARACTERISTICS:
        (A) LENGTH: 55 amino acids
        (B) TYPE: amino acid
        (D) TOPOLOGY: linear (i i) MOLECULE TYPE: peptide (i x) FEATURE:
    (A) NAME/KEY: Modified-site
    (B) LOCATION: 8
    (D) OTHER INFORMATION: /note= "Ornithine"

(i x) FEATURE:
    (A) NAME/KEY: Modified-site
    (B) LOCATION: 16
    (D) OTHER INFORMATION: /note= "Norvaline"

(i x) FEATURE:
    (A) NAME/KEY: Modified-site
    (B) LOCATION: 32
    (D) OTHER INFORMATION: /note= "Ornithine"

(i x) FEATURE:
    (A) NAME/KEY: Modified-site
    (B) LOCATION: 40
    (D) OTHER INFORMATION: /note= "Norvaline"

(i x) FEATURE:
    (A) NAME/KEY: Modified-site
    (B) LOCATION: 48
    (D) OTHER INFORMATION: /note= "Norleucine"

(x i) SEQUENCE DESCRIPTION: SEQ ID NO:47:

```
Lys Ala Thr Cys Thr Ala Asn Xaa Asp Ser Pro Asp Ala Glu Leu Xaa
 1               5                   10                  15

Glu Ala Asn Leu Leu Trp Arg Asn Glu Met Gly Gly Asn Ile Thr Xaa
              20                  25                  30

Val Glu Ser Glu Asn Lys Val Xaa Ile Leu Asp Ser Phe Asp Pro Xaa
              35                  40                  45
```

```
          Val  Ala  Glu  Glu  Asp  Glu  Arg
                50                  55
```

( 2 ) INFORMATION FOR SEQ ID NO:48:

( i ) SEQUENCE CHARACTERISTICS:
        ( A ) LENGTH: 35 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:48:

```
Lys  Lys  Lys  Cys  Asp  Glu  Leu  Ala  Ala  Lys  Leu  Val  Ala  Thr  Asp  Ala
 1              5                        10                       15
Leu  Met  Thr  Gly  Tyr  Thr  Gly  Asp  Phe  Asp  Ser  Val  Ile  Asp  Cys  Asn
               20                       25                       30
Thr  Cys  Val
          35
```

( 2 ) INFORMATION FOR SEQ ID NO:49:

( i ) SEQUENCE CHARACTERISTICS:
        ( A ) LENGTH: 44 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:49:

```
Gly  Arg  His  Leu  Ile  Phe  Cys  His  Ser  Lys  Lys  Cys  Asp  Glu  Leu
 1              5                        10                       15
Ala  Ala  Lys  Leu  Val  Ala  Thr  Asp  Ala  Leu  Met  Thr  Gly  Tyr  Thr  Gly
               20                       25                       30
Asp  Phe  Asp  Ser  Val  Ile  Asp  Cys  Asn  Thr  Cys  Val
               35                       40
```

( 2 ) INFORMATION FOR SEQ ID NO:50:

( i ) SEQUENCE CHARACTERISTICS:
        ( A ) LENGTH: 54 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:50:

```
Lys  Ala  Ile  Pro  Leu  Glu  Val  Ile  Lys  Gly  Gly  Arg  His  Leu  Ile  Phe
 1              5                        10                       15
Cys  His  Ser  Lys  Lys  Cys  Asp  Glu  Leu  Ala  Ala  Lys  Leu  Val  Ala
               20                       25                       30
Thr  Asp  Ala  Leu  Met  Thr  Gly  Tyr  Thr  Gly  Asp  Phe  Asp  Ser  Val  Ile
               35                       40                       45
Asp  Cys  Asn  Thr  Cys  Val
          50
```

( 2 ) INFORMATION FOR SEQ ID NO:51:

( i ) SEQUENCE CHARACTERISTICS:
        ( A ) LENGTH: 35 amino acids
        ( B ) TYPE: amino acid
        ( D ) TOPOLOGY: linear ( i i ) MOLECULE TYPE: peptide ( i x ) FEATURE:

(A) NAME/KEY: Modified-site
(B) LOCATION: 7
(D) OTHER INFORMATION: /note= "Norleucine"

(ix) FEATURE:
(A) NAME/KEY: Modified-site
(B) LOCATION: 17
(D) OTHER INFORMATION: /note= "Norleucine"

(ix) FEATURE:
(A) NAME/KEY: Modified-site
(B) LOCATION: 28
(D) OTHER INFORMATION: /note= "Norvaline"

(xi) SEQUENCE DESCRIPTION: SEQ ID NO:51:

Lys Lys Lys Cys Asp Glu Xaa Ala Ala Lys Leu Val Ala Thr Asp Ala
1               5                   10                  15

Xaa Met Thr Gly Tyr Thr Gly Glu Phe Asp Ser Xaa Ile Asp Cys Asn
            20                  25                  30

Thr Cys Val
        35

PEPTIDES EFFECTIVE FOR DIAGNOSIS AND DETECTION OF HEPATITIS C INFECTION

CROSS REFERENCE TO RELATED INVENTIONS

This is a continuation-in-part application of application Ser. No. 08/333,573 filed Nov. 1, 1994, now abandoned.

FIELD OF THE INVENTION

The present invention relates to novel linear and branched peptides specific for the diagnosis and prevention of hepatitis C virus (HCV) infection. More particularly, the present invention is directed to linear and branched synthetic peptides containing at least one antigenic site which is effective for detecting HCV-associated antibodies in patients using immunoassay techniques. In some cases, these peptides are also library peptides with degenerate amino acid positions. Preferred mixtures for detection of HCV antibodies are provided as well as a novel spliced peptide useful for blocking the non-specific reactivity of certain NS-3 conformational epitopes.

BACKGROUND OF THE INVENTION

Non-A, non-B hepatitis (NANBH) caused by HCV remains the most common form of post-transfusion hepatitis, imposing a strong need for sensitive and specific diagnostic screening methods to identify potential blood donors and other persons who may be carriers of the virus and able to transmit the disease. Thus, accurate screening methods are needed to permit removal of contaminated blood and blood products from the blood supply with a high degree of confidence.

The etiological agent HCV has been cloned and identified by several groups [Houghton et al., EP 0318216, published 5/1989; Okamoto et al. (1990) Jpn. J. Exp. Med. 60:167; Houghton et al., EP 0388232, published September 1990; and Kato et al. (1990) Proc. Natl. Acad. Sci. USA 87:9524; Arima et al. (1989a) Gastroenterologia Japonica 24:540; Reyes et al. (1990) Science 247:1335; Arima et al. (1989b) Gastroenterologia Japonica 24:545; Maeno et al. (1990) Nucleic Acids Res. 18:2685].

The HCV genome is about 10 kilobases (kb) in length and encodes a single polyprotein which is processed into structural and non-structural proteins. From the N terminus, the polyprotein includes the capsid and envelope proteins of the structural region and the NS-1 to NS-5 proteins of the non-structural region.

While some of the antigenic regions of HCV have been identified, peptides and recombinant proteins from these regions exhibit a variable degree of sensitivity and selectivity in detection and diagnosis of HCV carriers. Antigenic regions have been reported in the core, or capsid, protein [Wang, U.S. Pat. Nos. 5,106,726 and 5,436,126; Hosein et al. (1991) Proc. Natl. Acad. Sci. USA 88:3647; Okamoto et al. (1990) Jap. J. Exp. Med. 60:223; Takahashi et al. (1992) J. Gen. Virol. 73:667; Kotwal et al. (1992) Proc. Natl. Acad. Sci. USA 89:4486; Houghton, U.S. Pat. No. 5,350,671]; in the envelope, NS-1, NS-2 and NS-3 proteins [Wang et al., EP 0468527, published Jan. 29, 1992]; in the NS-3 protein [PCT/US94/07088; WO 93/09253; EP 0388232] in the NS-4 protein [Houghton (1989); Kuo et al. (1989) Science 244:362; U.S. Pat. Nos. 5,106,726 and 5,436,126] and NS-5 protein [Maeno et al. (1990) Nucleic Acids Res. 18:2685; Wang (1992)].

In addition to HCV-derived antigens, there exist other HCV-associated antigens that appear to be encoded by a host cellular sequence. One such antigen, known as the GOR epitope, is reactive with sera from individuals who are PCR positive for HCV [Mishiro et al. (1990) Lancet 336:1400].

Serological analysis has been used to map antigenic sites within certain HCV antigenic regions as described in Wang (1992) and U.S. Pat. No. 5,106,726. These mapping studies employed synthetic peptides to screen well-characterized HCV serum panels and permitted identification of highly immunoreactive HCV antigenic sites.

The demonstration that synthetic peptides are efficacious for detection of antibodies to HCV has led to numerous studies using short synthetic peptides to characterize antigenic sites. For example, the Pepscan technique has been applied to the entire HCV-1 genome to begin elucidation of immunoreactive sites (Chien et al., WO 93/00365).

In the core protein, an immunodominant antigenic site located within amino acid residues 21–45 has been described [Nagayama et al. (1994) J. Med. Virol. 42:311–7; Siemoneit et al. (1994) Hybridoma 13:9–13; Ferroni et al. (1993) J. Clin. Microbiol. 31:1586–91; Ishida et al. (1993) J. Clin. Microbiol. 31:936–40]. [Note: the amino acid numbering system herein refers to the HCV-1 polyprotein numbering system]. Human monospecific antibodies to bind a peptide corresponding to core residues 33–50 [Akatsuka et al. (1993) Hepatoloogy 18:503–10], and the binding site of a human monoclonal antibody directed against core was mapped to residues 34–45 [Cerino et al. (1993) J. Immunol. 151:7005–15]. Mouse monoclonal antibodies which bind to core residues 26–45 have been described [Gonzalez-Peralta et al. (1994) J. Hepatol. 20: 143–7]. Another antigenic site at the N-terminus of core has been delineated at residues 1–18 by synthetic peptide studies [Sallberg et al. (1992a) J. Clin. Microbiol. 30:1989–94; Sallberg et al. (1992b) Immunol. Lett. 33:27–33]. Additional antigenic peptides were identified between these two sites at residues 11–28 [Sallberg, (1992a)] and 7–21 [Ferroni]. Further antigenic sites are found in peptides consisting of core residues 1–84 and 9–177 [U.S. Pat. No. 5,350,671].

In NS-3, a conformational epitope was identified in the C-terminal 100 amino acids of the c-33c clone [Kink et al. WO 93/09253]. A human monoclonal antibody specific for this immunodominant antigenic site also bound to the C-terminus of NS-3 [Mondelli et al. (1994) J. Virol. 68:4829–36; Habets et al., WO 94/14974]. Hosein et al. identified an NS-3 conformational epitope at residues 1378–1459 [PCT/US94/07088].

Synthetic peptide studies located two epitopes in the NS-4 protein at amino acid residues 1661–1708 and 1710–1728 [Simmonds et al. (1993) J. Clin. Microbiol. 31:1493–503]. Murine monoclonal antibodies bound to residues 1700–1705 [Gonzales-Peralta, supra], and a human monoclonal antibody directed against the NS-4 protein was reported to bind to residues 1688–1705 [Cerino et al. (1991) J. Immunol. 147:2692–6].

Many proteins from infectious agents, or at least sites on those proteins, exhibit strain variation at the sequence level. For example, at a given time or in a particular geographic locale, a particular antigen may contain one or more point mutations relative to an arbitrary prototype strain. Dynamic variation can thereby create an extremely complex antigenic profile at such a site for which sensitive or specific detection can be increasingly difficult as the site "drifts" further from the prototype. Accordingly, complex antigens can provide a simplified means to detect multiple strains.

For HCV, thus far, combinations of synthetic peptides from multiple proteins or regions of HCV have proven effective as diagnostic tests for HCV [Ishida; Wang (1992); PCT/US94/07088]. However useful, such tests only represent sequences of a single strain. The known HCV sequence variability [Bukh et al. (1993) *Proc. Natl. Acad. Sci. USA* 90:8234–8] can still pose a problem for sensitive antibody detection whether with peptide-based tests or with a recombinant protein-based test. A synthetic peptide test designated as KCL-163 based on a Japanese HCV strain proved both more sensitive and more specific than a C100-3 test (based on the HCV-1 strain) in a Japanese population [Kawano et al. (1991) *Gastroenterol. Jpn.* 26:218–20]. HCV-1 clones 5-1-1, C-33c, and C-22 in a RIBA format detected antibody from type II HCV-infected sera better than from type I HCV-infected sera [Alonso et al. (1994) *J. Clin. Microbiol.* 32:211–2], whereas the C-100-3 was more sensitive for type I than for type II serum [Nagayama et al. (1993) *J. Clin. Invest.* 92:1529–33].

Further, type-specific synthetic peptides from NS-4, can be used to discriminate among HCV genotypes [Simmonds]. However, a single amino acid substitution in a core peptide (amino acids 101–108) of an HCV variant decreased reactivity with eight different HCV-1 sera [Sallberg (1992a)].

The present invention provides peptides which are sensitive and selective for the detection of HCV antibodies and, if desired, can accommodate strain-related antigenic variation through the use of peptide libraries.

SUMMARY OF THE INVENTION

The present invention is directed to a peptide composition comprising at least one linear or at least one branched peptide represented by the formula (peptide)–Y (peptide)$_2$X (peptide)$_4$X$_2$X (peptide)$_8$X$_4$X$_2$X (peptide)$_{16}$X$_8$X$_4$X$_2$X wherein Y is an OH or NH$_2$ group on the carboxyl group of the C terminal amino acid of (peptide) and X is an amino acid or an amino acid analog having two amino groups and one carboxyl group, each group capable of forming a peptide bond linkage. In accordance with this invention the peptide moiety, (peptide), is specifically immunoreactive with HCV-associated antibodies, and comprises an amino acid sequence selected from the group consisting of SEQ ID NOS:5 to 34 and 37–47 (see Tables 1, 3, 5, 7 and 13) or is one of the peptides of Formulas I–IX containing the particular substitutions and/or degenerate positions as described in the "Detailed Description of the Invention". Preferred mixtures of peptides include Mixtures A–E.

Another aspect of the invention provides a method of detecting antibodies to HCV or diagnosis of HCV infection by using an immunoeffective amount of the subject peptide composition in an immunoassay procedure, and particularly in an ELISA procedure, or a passive hemagglutination (PHA) assay. Immunoassays and kits for the detection and diagnosis of HCV infection are also provided.

A further aspect of the invention is directed to a peptide composition comprising a linear "spliced" peptide, its conjugates and its polymers that block non-specific reactivity of certain NS-3 conformational epitopes in HCV immunoassays, wherein the C terminal amino acid of the peptide is a carboxylic acid or carboxyl amide, and the peptide comprises an amino acid sequence selected from the group consisting of SEQ ID NOS:48–50 or is an analog of the spliced peptide having an amino acid sequence of a strain/isolate of HCV from the corresponding NS-3 regions of the spliced peptide (see Table 13). Likewise, the spliced peptides can be modified to contain substituted, deleted and degenerate positions and include preferred peptides of SEQ ID NO:51 and Formula X.

The spliced peptides are used to improve specific performance in immunoassays for detection of HCV antibodies or diagnosis of HCV infection in a subject by providing a first peptide composition containing a peptide or a protein having an NS-3 conformational epitope, such as the peptide compositions and mixtures described hereinabove; contacting an effective amount of that first peptide composition with a serum, tissue, tissue extract or a body fluid from the subject in the presence of, or after treatment with, an effective amount of the subject spliced peptide composition for a time sufficient to form a complex between the first peptide composition and any antibody in the serum, the tissue, the tissue extract or the fluid; and subjecting the complex to a detecting means. In a preferred embodiment the spliced peptide composition is present in the specimen diluent. Preferred immunoassay procedures using the spliced peptide include ELISA procedures and passive hemagglutination (PHA) assays. Immunoassays and kits for the detection and diagnosis of HCV infection using the spliced peptide are also provided.

DETAILED DESCRIPTION OF THE INVENTION

Figure 1:
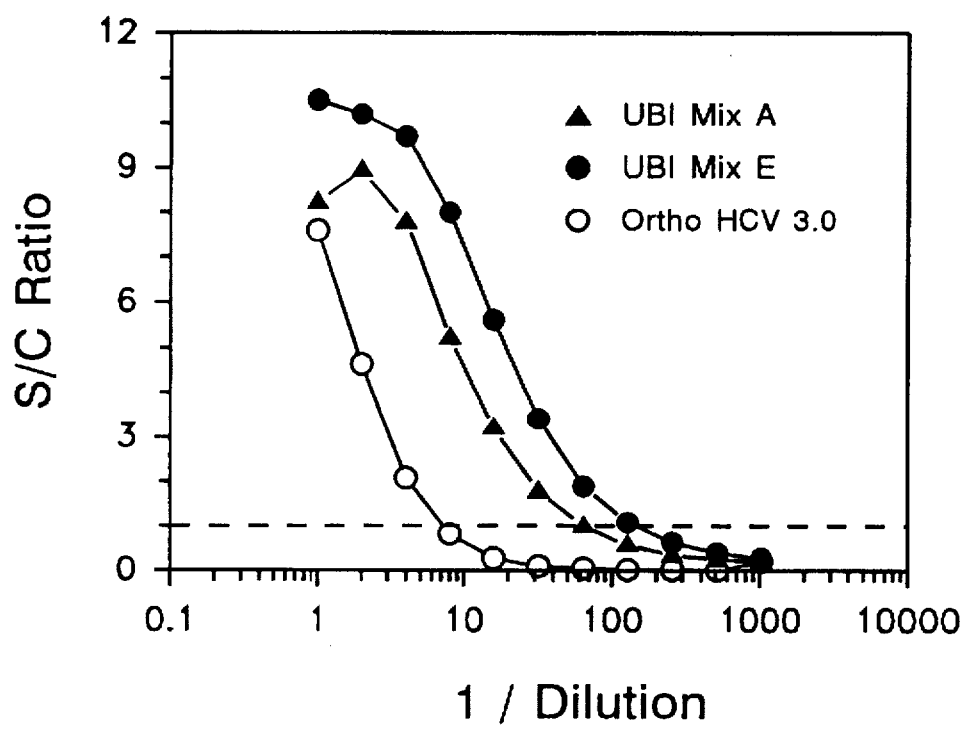
FIG. 1 graphically depicts the immunoreactivity of a dilution series of human monoclonal antibody (B12.F8) specific for HCV core with (▲) Mixture A peptides (Example 6), (●) Mixture E peptides (Example 6) and (○) a commercially available HCV antibody detection kit (Ortho HCV 3.0; Ortho Diagnostic Systems, Inc.).

In accordance with the present invention, extensive serological analysis has led to the refinement and further definition of immunoreactive peptides that are useful in the detection of HCV antibodies and diagnosis of HCV infection. It has been discovered that synthetic peptides containing multiple substitutions of natural and unnatural amino acids in a prototype HCV sequence are highly effective for detection and diagnosis of HCV infection. Likewise, these multiply-substituted peptides can contain degenerate positions with sequence variability to provide high selectivity and sensitivity for multiple strains of HCV. Accordingly, the preferred peptides of this invention are those of SEQ ID NO:5–34 and 37–47 as listed in Tables 1, 3, 5, 7 and 13.

All the peptides of the invention are designated and named by their respective sequence identification numbers.

Each of these peptides has a particular pattern of substitutions, deletions or degenerate positions in its peptide moiety relative to one of the six prototype sequences set forth below:

Ala — Arg — Pro — Asp — Tyr — Asn — Pro — Pro — Leu — Val — Glu — Thr — Trp — Lys — Lys —
Pro — Asp — Tyr — Glu — Pro — Pro — Val — Val — His — Gly — Cys — Pro — Leu — Pro — Pro —
Pro — Lys — Ser — Pro — Pro — Val — Pro — Pro — Pro — Arg — Lys — Lys — Arg — Thr,
(SEQ ID NO:1),

Ser — Gly — Lys — Pro — Ala — Ile — Ile — Pro — Asp — Arg — Glu — Val — Leu — Tyr — Arg —
Glu — Phe — Asp — Glu — Met — Glu — Glu — Cys — Ser — Gln — His — Leu — Pro — Tyr — Ile —
Glu — Gln — Gly — Met — Met — Leu — Ala — Glu — Gln — Phe — Lys — Gln — Lys — Ala — Leu —
Gly — Leu,

IIH (SEQ ID NO:2),

Ser — Thr — Ile — Pro — Lys — Pro — Gln — Arg — Lys — Thr — Lys — Arg — Asn — Thr — Asn —
Arg — Arg — Pro — Gln — Asp — Val — Lys — Phe — Pro — Gly — Gly — Gly — Gln — Ile — Val —
Gly — Gly — Val — Tyr — Leu — Leu — Pro — Arg — Arg — Gly — Pro — Arg — Leu — Gly — Val —
Arg — Ala — Thr — Arg — Lys — Thr — Ser — Glu — Arg — Ser — Gln — Pro — Arg — Gly — Arg —
Arg,

VIIIE (SEQ ID NO:3),

Lys — Ala — Ile — Pro — Leu — Glu — Val — Ile — Lys — Gly — Gly — Arg — His — Leu — Ile —
Phe — Cys — His — Ser — Lys — Lys — Lys — Cys — Asp — Glu — Leu — Ala — Ala — Lys — Leu —
Val — Ala — Leu — Gly — Ile — Asn — Ala — Val — Ala — Tyr — Tyr — Arg — Gly — Leu — Asp —
Val — Ser — Val — Ile — Pro — Thr — Ser — Gly — Asp — Val — Val — Val — Val — Ala — Thr —
Asp — Ala — Leu — Met — Thr — Gly — Tyr — Thr — Gly — Asp — Phe — Asp — Ser — Val — Ile —
Asp — Cys — Asn — Thr — Cys — Val,
(SEQ ID NO:4),

Lys — Gln — Lys — Ala — Leu — Gly — Leu — Leu — Gln — Thr — Ala — Ser — Arg — Gln — Ala —
Glu — Val — Ile — Ala — Pro — Ala — Val — Gln — Thr — Asn — Trp — Gln — Lys — Leu — Glu —
Thr — Phe — Trp — Ala — Lys — His — Met — Trp — Asn — Phe, and
V (SEQ ID NO:35), Lys — Ala — Thr — Cys — Thr — Ala — Asn — His — Asp — Ser — Pro — Asp — Ala — Glu — Leu —
Ile — Glu — Ala — Asn — Leu — Leu — Trp — Arg — Gln — Glu — Met — Gly — Gly — Asn — Ile —
Thr — Arg — Val — Glu — Ser — Glu — Asn — Lys — Val — Val — Ile — Leu — Asp — Ser — Phe —
Asp — Pro — Leu — Val — Ala — Glu — Glu — Asp — Glu — Arg
pep12 (SEQ ID NO:36).

As used herein a position in a prototype sequence wherein one amino acid is replaced by another is termed a "substituted position". Similarly a position in a prototype sequence wherein an amino acid thereof is not present is termed a deleted position. Finally, a position in a prototype sequence wherein a single amino acid is replaced by a mixture of 2 or more amino acids during peptide synthesis (i.e. as for library peptides described below) is termed a degenerate position.

The peptides of this invention can be linear or branched, and the invention includes polymers, conjugates and mixtures of the peptides. Some peptides are hybrids of one or more HCV antigens from different HCV proteins, e.g. NS-4 and core.

Further some of the peptides contain degenerate positions, i.e. these peptides represent "libraries" of peptides as generally described in U.S. Ser. No. 143,412, filed Oct. 26, 1993 (the'412 application). ["Library peptides"as used herein are also referred to as "structured synthetic antigen libraries" or "SSAL" in the '412 application].

For library peptides, degenerate amino acid positions are those positions of known sequence variability, i.e., generated by strain to strain differences in HCV isolates. The degenerate positions thus contain any one of two or more amino acid residues. The possible residues for a given position are determined from known sequence variations which occur at that position in the sequence of the peptide. The proportion of amino acids used during synthesis at a particular position can be represented by either the frequency at which the given residues appear in the known variants, or by a simple equimolar distribution of the possible amino acids at that position. It should be noted that for this invention, not every sequence position susceptible to strain variation needs to be used.

As used herein a linear peptide can have from about 30 to about 100 amino acids, preferably about 40 to about 85 amino acids. However, the linear peptide can also consist of as few as 8 or 9 residues.

The subject peptides can have a few more amino acids, including unnatural amino acids, added to the terminal amino acids. For example, the sequence KKK (Lys-Lys-Lys) can be added to the amino terminus of any of these peptides. For branched peptides, an M (methionine) residue can be placed at the carboxyl terminus of the peptide moiety, i.e. between the peptide moiety and the branch structure. Similarly the peptides can have a cysteine at the C terminus to facilitate using the thiol group of cysteine to form a covalent bond to an electrophilic group such as $N^{\alpha}$-chloroacetyl-modified amino acid or a maleimide-derivatized $\alpha$- or $\epsilon$-$NH_2$ group of a lysine residue that is attached to the N-terminus of another peptide.

HCV is known to have frequent mutations. Several variant strains/isolates are known to exist, such as PT, J, J1and J4[Houghton, 1989; Okamoto, 1990; Houghton, 1990; and Kato, 1990] and it is expected that other variant strains also exist (Bukh). Adjustments for conservative substitutions arising from strain variation can be made in the prescribed sequences, provided that the pattern of substituted, deleted, or degenerate positions in a given peptide are maintained. In this way, the peptides of this invention can accommodate the strain-to-strain variation existing among different isolates of HCV via changes which do not affect antigenicity of the peptides.

Accordingly, the changes that are contemplated within the scope of the invention preserve the immunoreactivity of the peptides with HCV antibodies but do not affect the pattern of substituted, deleted or degenerate positions. The changes can consist of substitutions, insertions, deletions or degeneracies at about 2 to about 5 positions, or alternatively at up to about 10% of the positions in a peptide from Tables 1, 3, 5, 7 or 13. Moreover, the contemplated changes are derived from known HCV strains.

Such peptides in accordance with this invention are synthesized and tested against an HCV serum panel to determine the immunoreactivity of the peptide as described herein below.

The subject peptides can also be used to form conjugates, i.e., the peptides can be coupled directly or indirectly, by methods known in the art, to carrier proteins such as bovine serum albumin (BSA), human serum albumin (HSA), or to red blood cells or latex particles.

As used herein, natural amino acids are the 20 amino acids commonly found in proteins (i.e. alanine, aspartic acid, asparagine, arginine, cysteine, glycine, glutamine, glutamic acid, histidine, isoleucine, leucine, lysine, methionine, phenylalanine, proline, serine, threonine, tyrosine, tryptophan and valine). As used herein the natural amino acids also include the D- and L- forms of such amino acids.

As used herein "unnatural amino acids" include both D- and L- forms of any other amino acids whether found in a protein, whether found in nature or whether synthetically produced. Unnatural amino acids can include, but are not limited to, β-alanine, ornithine, norleucine, norvaline, hydroxyproline, thyroxine, gamma-amino butyric acid, homoserine, citrulline and the like.

The linear peptides of this invention are represented by the formula

[peptide]-Y wherein Y is -OH or $-NH_2$, and include mixtures, conjugates and polymers of these linear peptides. The peptides comprise at least one antigenic site which is specifically immunoreactive with antibodies against HCV.

The branched peptides of the present invention are represented by one of the formulae:

$[peptide]_2X$ $[peptide]_4X_2X$ $[peptide]_8X_4X_2X$ $[peptide]_{16}X_8X_4X_2X$ wherein X is an amino acid or an amino acid analog having two amino groups and one carboxyl group, each group capable of forming a peptide bond linkage. Preferably X is lysine or a lysine analog such as ornithine. The amino acid analog can be an α-amino acid, a β-amino acid, or any other either natural or non-natural amino acid with two amino groups and one carboxyl group available for forming peptide bonds. Preferred branched peptides of the invention are dimers, tetramers and octamers, especially those having a branching core structure composed of lysine, i.e. where X is lysine. Branched dimers and octamers are especially preferred.

The peptide moiety of the linear or branched peptides can vary in length from about 8 or 9 to about 100 amino acids residues. Preferably the peptide moieties contain about 9 to about 60 amino acid residues.

The preferred peptides of the present invention are those branched or linear peptides having a sequence of SEQ ID NOS:5–34 or 37–47 as provided in Tables 1, 3, 5, 7 and 13.

Another aspect of this invention relates to peptide compositions having one or more of the peptides represented by Formulas I–IX.

Formula I peptides are those which substantially retain the frame of the 81 amino acid prototype sequence of SEQ ID NO:4, which are immunoreactive with HCV NS-3 antibodies and which consist of the following substituted, deleted or degenerate positions:

position 3: norvaline, position 7: norvaline or Val:Ala:Thr:Phe:Tyr:Nvl at 3:3:1:1:1:1 ratio, position 8: valine or norvaline, position 16: norvaline, position 20: arginine, position 26: norleucine, position 33: norleucine, position 39: serine, position 46: norvaline, position 52: alanine, position 60: serine, position 63: norleucine, position 68: serine, and position 74: norvaline.

Nvl is the abbreviation for norleucine. The positions referred to herein in Formulas I–IX are relative to those in SEQ ID NOS:1–4, 35 and 36.

Formula II peptides are those peptides which substantially retain the frame of the 61 amino acid prototype sequence of SEQ ID NO:3, which are immunoreactive with HCV core antibodies and which consist of the following substituted or degenerate positions:

position 4: Pro:Gly at 9:1 ratio, position 8: ornithine, position 10: Thr:Asn at 7:3 ratio, position 16: lysine, position 21: norvaline, position 24: hydroxyproline, position 30: norvaline, position 36: valine or norleucine, position 43: norleucine, position 45: leucine, position 48: Thr:Pro at 9:1 ratio, position 52: threonine or Thr:Ala:Glu:Lys at 1:1:1:1 ratio, and position 57: hydroxyproline.

Formula III peptides are those peptides which substantially retain the frame of the 47 amino acid prototype sequence SEQ ID NO:2 followed by the 9 amino acid prototype sequence of residues 21 to 29 of SEQ ID NO:3, which are immunoreactive with HCV NS-4 or core antibodies and which consist of the following substituted or degenerate positions:

position 1: Ser:Asn at 8:2 ratio, position 2: Gly:Asp:Gln at 8:1:1 ratio, position 3: Lys:Arg at 6:4 ratio, position 4: Pro:Val:Ala at 8:1:1 ratio, position 5: threonine, position 6: Ile:Val at 6:4 ratio, position 7: Ile:Val:Ala at 6:2:2 ratio, position 10: Arg:Lys at 8:2 ratio, position 12: norvaline, position 15: Arg:Gln:Glu at 3:5:2 ratio, position 16: Glu:Ala at 8:2 ratio, position 19: aspartate, position 22: aspartate, position 24: Ser:Ala at 4:6 ratio, position 25: Gln:Ser at 4:6 ratio, position 26: His:Lys:Arg at 8:1:1 ratio, position 27: Leu:Ala at 8:2 ratio, position 28: Pro:Ala at 8:2 ratio, position 29: Tyr:Leu at 8:2 ratio, position 30: norleucine or norvaline, position 31: aspartate, position 32: Gln:Glu at 8:2 ratio, position 34: Met:Gln at 8:2 ratio, position 35: Met:Gln:Arg at 4:4:2 ratio, position 36: Leu:Met:Ile at 8:1:1 ratio, position 39: asparagine, position 40: Phe:Leu at 8:2 ratio, position 42: Gln:Ser at 8:2 ratio, position 44: Ala:Ile at 8:2 ratio, or position 45: valine, and position 55: asparagine.

Formula IV peptides are those which substantially retain the frame of the 44 amino acid prototype sequence of SEQ ID NO:1, which are immunoreactive with HCV NS-5 antibodies and which consist of the following substituted or degenerate positions: position 2: ornithine, position 8: Pro:Leu:Val at 8:1:1 ratio, position 10: norvaline, position 12: Thr:Ser:Pro at 5:4:1 ratio, position 15: Lys:Asp:Arg at 4:4:2 ratio, position 17: glutamate, position 19: Glu:Val:Gln at 5:4:1 ratio, position 21: Pro:Ala at 9:1 ratio, position 22: Val:Thr at 8:2 ratio, position 23: norvaline, position 24:

His:Leu:Ala at 8:1:1 ratio, position 27: Pro:Ala at 8:2 ratio, position 30: Pro:Ser at 9:1 ratio, position 31: hydroxyproline, position 32: Lys:Pro:Arg at 8:1:1 ratio, position 33: Ser:Ala:Lys: Gln at 4:4:1:1 ratio, position 34: Pro:Thr at 8:2 ratio, position 36: Val:Ile: Thr at 5:4:1 ratio, position 37: hydroxyproline, position 41: Lys:Arg at 4:6 ratio, position 42: Lys:Arg at 7:3 ratio, and position 44: Thr:Ala at 9:1 ratio.

Formula V peptides are those which substantially retain the frame of the 52 amino acid prototype sequence of residues 1 to 52 of SEQ ID NO:3, which are immunoreactive with HCV core antibodies and which consists of the following substituted positions:

position 8: ornithine or lysine, position 16: ornithine or lysine, position 24: hydroxyproline, position 29: norvaline, position 37: hydroxyproline, position 43: norleucine, and position 45: norvaline or leucine.

The Formula V peptides can further consist of one or more of the following substituted or degenerate positions: position 4: Pro:Gly at 9:1 ratio, position 10: Thr:Asn at 7:3 ratio, position 21: norvaline, position 30: norvaline, position 36: valine or norleucine, position 48: Thr:Pro at 9:1 ratio and position 52: threonine or Thr:Ala:Glu:Lys at 1:1:1:1 ratio.

Formula VI peptides are those which substantially retain the frame of the 47 amino acid prototype sequence of SEQ ID NO:2, which are immunoreactive with HCV NS-4 antibodies and which consists of the following substituted positions:

position 1: asparagine, position 2: glutamine, position 3: arginine, position 4: hydroxyproline, position 5: serine or threonine, position 12: norvaline or isoleucine, position 15: ornithine, position 22: aspartate, position 27: norvaline, position 31: aspartate, position 39: asparagine, and position 45: norvaline or valine.

The Formula VI peptides can further consist of one or more of the following substituted or degenerate positions:

position 6: Ile:Val at 6:4 ratio, position 7: Ile:Val:Ala at 6:2:2 ratio, position 10: Arg:Lys at 8:2 ratio, position 16: Glu:Ala at 8:2 ratio, position 19: aspartate, position 24: Ser:Ala at 4:6 ratio, position 25: Gln:Ser at 4:6 ratio, position 26: His:Lys:Arg at 8:1:1 ratio, position 28: Pro:Ala at 8:2 ratio, position 29: Tyr:Leu at 8:2 ratio, position 30: norleucine or norvaline, position 32: Gln:Glu at 8:2 ratio, position 34: Met:Gln at 8:2 ratio, position 35: Met:Gln:Arg at 4:4:2 ratio, position 36: Leu:Met:Ile at 8:1:1 ratio, position 40: Phe:Leu at 8:2 ratio, position 42: Gln:Ser at 8:2 ratio and position 44: Ala:Ile at 8:2 ratio.

Formula VII peptides are those which substantially retain the frame of the 44 amino acid prototype sequence of SEQ ID NO:1, which are immunoreactive with HCV NS-5 antibodies and which consists of the following substituted positions:

position 2: ornithine, position 10: norvaline, position 17: glutamate, position 23: norvaline, position 31: hydroxyproline and position 37: hydroxyproline.

The Formula VII peptides can further consist of one or more of the following degenerate positions:

position 8 Pro:Leu:Val at 8:1:1 ratio, position 12: Thr:Ser: :Pro at 5:4:1 ratio, position 15: Lys:Asp:Arg at 4:4:2 ratio, position 19: Glu:Val:Gln at 5:4:1 ratio, position 21: Pro:Ala at 9:1 ratio, position 22: Val:Thr at 8:2 ratio, position 24: His:Leu:Ala at 8:1:1 ratio, position 27: Pro:Ala at 8:2 ratio, position 30: Pro:Ser at 9:1 ratio, position 32: Lys:Pro:Arg at 8:1:1 ratio, position 33: Ser:Ala:Lys: Gln at 4:4:1:1 ratio, position 34: Pro:Thr at 8:2 ratio, position 36: Val:Ile: Thr at 5:4:1 ratio, position 41: Lys:Arg at 4:6 ratio, position 42: Lys:Arg at 7:3 ratio, and position 44: Thr:Ala at 9:1 ratio.

Formula VIII peptides are those which substantially retain the frame of the 40 amino acid prototype sequence of SEQ ID NO:35, which are immunoreactive with HCV NS-4 antibodies and which consists of the following substituted positions:

position 8: norleucine, position 13: ornithine, position 20: hydroxyproline, position 28: arginine and position 35: ornithine.

Formula IX peptides are those which substantially retain the frame of the 55 amino acid prototype sequence of SEQ ID NO:36, which are immunoreactive with HCV NS-5 antibodies and which consists of the following substituted positions:

position 8: ornithine, position 16: norvaline, position 24: asparagine, position 32: ornithine, position 40: norvaline and position 48: norleucine.

The peptides represented by Formulas I–IX can be linear or branched and the invention includes polymers, conjugates and mixtures of these peptides in accordance with those embodiments as described herein.

As used herein, an "HCV NS-3 antibody" includes an antibody or a serum or plasma sample containing antibodies which immunoreacts with or bind to peptide 4 (SEQ ID NO:4). As used herein an "HCV core antibody" includes an antibody or a serum or plasma sample containing antibodies which immunoreacts with or bind to peptide 3 (aka VIIIE; SEQ ID NO:3). As used herein an "HCV NS-4 antibody" is an antibody or a serum or plasma sample containing antibodies which immunoreacts with or bind to peptide 2 (aka IIIH; SEQ ID NO:2). As used herein an "HCV NS-5 antibody" includes an antibody or a serum or plasma sample containing antibodies which immunoreacts with or bind to peptide 1 (SEQ ID NO:1).

The peptide compositions of the present invention can be composed of one or more of the subject peptides. Preferably such compositions contain from one to 10 peptides, and, more preferably from one to four peptides and even more preferably from one to six peptides.

In a preferred embodiment, the peptide compositions of the present invention include peptides 19, 25, 27, 28, 29, 33, 37, 38, 39, 43, 45, 46 and 47; and preferably peptides 19, 25, 29, 33, 37, 43, 45, 46 and 47; and most preferably peptides 19, 37, 43, 45, 46 and 47.

Moreover, the peptide compositions of the present invention include mixtures of peptides. The effective ratio of peptides for diagnosing or detecting HCV present in peptide compositions containing mixtures of the subject peptides can be readily determined by one of ordinary skill in the art. Typically, these ratios range from about 1 to about 50 on a per weight basis of peptide.

A preferred peptide composition for diagnosis and detection of HCV infection is selected from a mixture of peptides known as Mixture A, which includes peptides 25, 29, 33, and 19; Mixture B which includes peptides 25, 27, 33, and 19; Mixture C which includes peptides 33, 25, 19 and 28; Mixture D which includes peptides 19, 33, 38, 39 46 and 47; and Mixture E which includes peptides 19, 37, 43, 45, 46 and 47.

In a preferred embodiment Mixture A is coated at a weight ratio of 2:2:0.5:8 for peptides 25, 29, 33 and 19, respectively. In another preferred embodiment, Mixture E is coated at a weight ratio of 1.5:1:1:0.5:1:2 for peptides 43, 46, 37, 45, 47 and 19, respectively.

The peptide compositions, peptides and mixtures described herein above in the "Detailed Description of the Invention" are useful for the detection of antibodies to HCV in body fluids, and the diagnosis of HCV infection.

To determine the efficacy of the subject peptides in detecting and diagnosing HCV antibodies, the peptides are tested for their immunoreactivity with specimens previously selected through the screening of thousands of patient and normal sera for immunoreactivity with HCV. Such HCV-specific serum panels are commercially available and examples of serum panels and methods to select appropriate panel are provided in the Examples.

The strategy for serological validation depends on the expected characteristics of the target antigenic sites. For example, universal immunodominant sites, such as the gp41 transmembrane peptide of HIV-1, can be screened by a single representative serum sample from a patient known to be infected with the virus. Antigenic sites that are not recognized by all infected individuals, or those for which antibody is produced late or only transiently, must be screened by large panels of sera. While both methods of screening can be employed in the present invention to refine the antigenic analysis for HCV using the subject peptides, the latter method is particularly useful in assessing the subject peptides and peptide compositions for superior selectivity and sensitivity.

The identification of the antigenic sites is also dependent on the panel of sera used. The more closely the panel represents the population most likely to be seropositive for a site, the greater the chance that the antigenic site will be identified and thoroughly mapped. Hence, to extend the range of reactivity of an assay comprised of previously identified antigenic sites or epitopes, a large number of samples from individuals at risk of infection but seronegative against known antigens or epitopes should be employed for screening.

The process of "serological validation" is particularly difficult when the antigenic site to be identified elicit antibodies only in a subpopulation of an infected patient group. When such antigens become targets for identification, special attention must be paid to synthetic peptides which show very weak reactivity.

In this regard, the low background absorbance of synthetic peptides, especially peptides with unnatural amino acids, allows for the precise detection of weak reactivities. In some cases, absorbances of 50 mA versus background reading are of sufficient significance and can lead to the identification of important antigenic sites through successive refinement of the amino acid sequence of a peptide. With good laboratory practices, consistent and reliable results can be obtained when working in the range of absorbances below 200–300 mA.

The peptides can be readily synthesized using standard techniques, such as the Merrifield method of synthesis [Merrifield (1963) *J. Am. Chem. Soc.* 85:2149–2154] and the myriad of available improvements on that technology, see e.g., *Synthetic Peptides: A User's Guide*, Grant, ed. (1992) W. H. Freeman & Co., New York, pp. 382; Jones (1994) *The Chemical Synthesis of Peptides*, Clarendon Press, Oxford, pp. 230.

Another problem which can be minimized by using peptides rather than recombinantly expressed proteins is the rate of false positive results caused by the presence of antigenic material co-purified with HCV recombinant proteins. For example, certain normal individuals have antibodies to *Escherichia coli* or yeast proteins which are cross reactive with the antigenic materials from the expression system used in recombinant-based diagnostic tests. Sera from such normal individuals can show a false positive reaction in such immunoassays which false reaction is eliminated in immunoassays of the present invention.

Moreover, because the peptide compositions of the present invention are synthetically prepared, the quality can be controlled and as a result, reproducibility of the test results can be assured. Also, since very small amounts of a peptide are required for each test procedure, and because the expense of preparing a peptide is relatively low, the cost of screening body fluids for antibodies to HCV and diagnosis of HCV infection is relatively low.

As a further advantage, the use of library peptides may provide the assay with a broader spectrum of reactivity against a greater number of HCV strains. In essence, degenerate positions of the library peptides represent an "open" diagnostic tool which accommodates the strain-specific sequence variation (and concomitant variation in antibody specificity) arising from multiple strains of HCV. Hence, library peptides can enhance the ability of the antigenic peptides to react with antibodies specific for a wider range of HCV variants.

The peptides and peptide compositions prepared in accordance with the present invention can be used to detect HCV antibodies and diagnose HCV infection by using them as the test reagent in an enzyme-linked immunoadsorbent assay (ELISA), an enzyme immunodot assay, a passive hemagglutination assay (e.g., PHA test), an antibody-peptide-antibody sandwich assay, a peptide-antibody-peptide sandwich assay, or other well-known immunoassays. In accordance with the present invention, any suitable immunoassay can be used with the subject peptides. Such techniques are well known to the ordinarily skilled artisan and have been described in many standard immunology manuals and texts, see for example, by Harlow et al. (1988) *Antibodies: A Laboratory Manual*, Cold Spring Harbor Laboratory Press, Cold Spring Harbor, N.Y., 726 pp. In a preferred embodiment, the immunoassay is an ELISA using a solid phase coated with the peptide compositions of the present invention. ELISA techniques are well known in the art. In another preferred embodiment the immunoassay is a PHA assay.

The immunoassays of the present invention are used to screen body fluids and tissues for the presence of HCV reactive antibody and thereby aid the practitioner in diagnosis of HCV infection. The body fluids which can be screened include blood and blood fractions (e.g. plasma and serum), saliva, or any other fluid which is suspected of containing antibodies against HCV.

Another aspect of the present invention is directed to a kit for the detection of HCV antibodies or diagnosis of HCV infection in mammalian body fluids (e.g. serum, tissue extracts, tissue fluids), in vitro cell culture supernatants, and cell lysates. The kit can be compartmentalized to receive a first container adapted to contain one or more of the peptides (i.e., a peptide composition) of this invention.

Preferably the kit of this invention is an ELISA or a PHA test kit for detection of HCV antibodies and thereby allow diagnosis of HCV infection. For an ELISA test kit, the kit contains (a) a container (e.g., a 96-well plate) having a solid phase coated with one of the subject peptide compositions; (b) a negative control sample; (c) a positive control sample; (d) specimen diluent and (e) antibodies to human IgG, which antibodies are labelled with a reporter molecule. If the reporter molecule is an enzyme, then the kit also contains a substrate for said enzyme.

In an exemplified use of the subject kit, a sample to be tested is contacted with a mammalian body fluid, diluted in sample diluent if necessary, for a time and under conditions for any antibodies, if present, to bind to the peptide contained in the container. After removal of unbound material (e.g. by washing with sterile phosphate buffered saline), the secondary complex is contacted with labelled antibodies to human IgG. These antibodies bind to the secondary complex to form a tertiary complex and, since the second antibodies are labeled with a reporter molecule, when subjected to a detecting means, the tertiary complex is detected. The reporter molecule can be an enzyme, radioisotope, fluorophore, bioluminescent molecule, chemiluminescent molecule, biotin, avidin, streptavidin or the like. For ELISA the reporter molecule is preferably an enzyme.

Another aspect of this invention relates to a peptide composition comprising a spliced peptide that blocks non-specific immunoreactivity of certain NS-3 conformational epitopes in HCV immunoassays. In general, the spliced peptides are soluble in aqueous buffer.

As a linear peptide, the peptide consists of an amino acid sequence selected from the group consisting of SEQ ID NOS:48–50 (Table 13) or an amino acid sequence of a strain/isolate of HCV from corresponding NS-3 regions of one of these peptides. This group of peptides is referred to as "spliced" because each peptide contains a large internal deletion in the NS-3 region. The peptides therefore contain a deletion of amino acids 33 to 57 of SEQ ID NO:4. Because residues 31–32 and 58–59 are the same (Val-Ala), these residues only occur once at the junction of the splice. A preferred peptide of the invention is the peptide of SEQ ID NO:48.

Serological analysis of this region has shown that this peptide can contain multiple substitutions of natural and unnatural amino acids in the prototype HCV sequence and remain highly effective at blocking non-specific reactivity of the NS-3 conformational epitope. Hence, the spliced peptides can have the particular pattern of substitutions, deletions or degenerate positions relative to its prototype sequence set forth below:

Lys-Lys-Lys-Cys-Asp-Glu-Leu-Ala-Ala-Lys-Leu-Val-Ala-Thr-Asp-Ala-Leu-Met-Thr-Gly-Tyr-Thr-Gly-Asp-Phe-Asp-Ser-Val-Ile-Asp-Cys-Asn-Thr-Cys-Val, (SEQ ID NO:48).

Hence, the spliced peptides can be represented by Formula X. Formula X peptides are those peptides which block non-specific reactivity of NS-3 conformational epitopes in HCV immunoassays, which substantially retain the frame of the 35 amino acid prototype sequence of SEQ ID NO:48, and which consist of the following substituted positions:

position 7: norleucine, 17: norleucine, position 24: glutamate, and position 28: norvaline.

In a preferred embodiment, the spliced peptide is the peptide of SEQ ID NO:51.

The prototype, analogue or modified spliced peptides can be conjugated to a carrier or polymerized as described hereinabove. When the peptide is polymerized in a branched form it can be represented by the formula:

$(peptide)_2X$ $(peptide)_4X_2X$ $(peptide)_8X_4X_2X$ $(peptide)_{16}X_8X_4X_2X$ wherein X is an amino acid or an amino acid analog having two amino groups and one carboxyl group, each group capable of forming a peptide bond linkage.

The linear portion of the spliced peptides (modified or unmodified) range in length as described above for the other peptides of the invention. Preferably, the spliced peptides have lengths that are about 30 to about 50 amino acids peptides. Similarly amino acids can be added at either termini of the spliced peptides as described herein above. Strain-to-strain variation can also be accommodated as described hereinabove.

The spliced peptides (including prototype,analog or modified peptides) are used in a method of detecting HCV antibodies or diagnosis of HCV infection in a subject which comprises (i) providing a first peptide composition containing a peptide or a protein having an NS-3 conformational epitope; (ii) contacting an effective amount of that first peptide composition with a serum, tissue, tissue extract or a body fluid from the subject in the presence of, or after pretreatment with, an effective amount of the subject spliced peptide composition in an immunoassay procedure for a time sufficient to form a complex between said first peptide composition and any antibody in the serum, the tissue, the tissue extract or the fluid, (iii) and subjecting the complex to a detecting means. Preferably the immunoassay procedure is an ELISA assay, a sandwich assay or a PHA assay.

The spliced peptide composition can be conveniently provided in the specimen diluent and is used in a concentration range of 5–100 μg/mL, and preferably at about 50 μg/mL. The spliced peptide concentration suitable for an individual assay can readily be determined by titrating the quantity of spliced peptide in the specimen diluent.

For this assay, the first peptide composition comprises a peptide having an NS-3 conformational epitope, wherein the peptide is selected from the group consisting of (i) peptide 4 (SEQ ID NO:4);

(ii) an analog peptide having an amino acid sequence of a strain/isolate of HCV in a region corresponding to said peptide 4;

(iii) a linear peptide wherein the C terminal amino acid of said peptide is a carboxylic acid or carboxylic amide, wherein the peptide is specifically immunoreactive with hepatitis C virus (HCV) antibodies, and wherein the peptide substantially retains the frame of the 81 amino acid prototype sequence of SEQ ID NO:4, which is immunoreactive with HCV NS-3 antibodies and which consists of the following substituted or degenerate positions:

position 3: norvaline, position 7: norvaline or Val:Ala:Thr:Phe:Tyr:Nvl at 3:3:1:1:1:1 ratio, position 8: valine or norvaline, position 16: norvaline, position 20: arginine, position 26: norleucine, position 33: norleucine, position 39: serine, position 46: norvaline, position 52: alanine, position 60: serine, position 63: norleucine, position 68: serine, and position 74: norvaline; and (iv) any one of peptides 5–21 (SEQ ID NOS:5–21). Any of these peptides can be conjugated to a carrier or polymerized. When the peptide is polymerized it is represented by the formula:

$(peptide)_2X$ $(peptide)_4X_2X$ $(peptide)_8X_4X_2X$ $(peptide)_{16}X_8X_4X_2X$ wherein X is an amino acid or an amino acid analog having two amino groups and one carboxyl group, each group capable of forming a peptide bond linkage. Finally the first peptide composition can be Mixture A, Mixture B, Mixture C, Mixture D or Mixture E.

Another aspect of the invention provides a kit for detection of HCV antibodies or diagnosis of HCV infection comprising a first container adapted to contain the peptide composition having an NS-3 conformational epitope and a second container adapted to contain specimen diluent comprising the spliced peptide composition of the invention. Preferably the kit is an ELISA test kit, a sandwich assay kit or PHA assay kit. An ELISA test kit for detection of HCV antibodies or diagnosis of HCV infection comprising (a) a container having a solid phase coated any one of the the first peptide compositions described in the preceding paragraph; and (b) specimen diluent comprising one of the subject spliced peptide compositions. In a preferred embodiment, the first peptide composition is Mixture E and the spliced peptide composition contains peptide 48 or 51. In a further embodiment the kit also contains (c) a negative control sample; (d) a positive control sample; and (e) antibodies to human IgG, said antibodies labeled with a reporter molecule. The kits are used as described hereinabove for kits with specimen diluent that lack the spliced peptide.

The examples serve to illustrate the present invention and are not to be used to limit the scope of the invention.

EXAMPLE 1

ELISA Assay Method

The wells of 96-well plates were coated separately for 1 hour at 37° with 5 µg/ml of peptide using 100 µL per well in 10 mM $NaHCO_3$ buffer, pH 9.5 unless noted otherwise.

The peptide-coated wells were incubated with 250 µL of 3% by weight of gelatin in PBS in 37° C. for 1 hour to block non-specific protein binding sites, followed by three washes with PBS containing 0.05% by volume of TWEEN 20 and dried. The test specimens containing HCV antibody positive patient sera were diluted 1:20 volume to volume with PBS containing 20% by volume normal goat serum, 1% by weight gelatin and 0.05% by volume TWEEN 20. 100 µL of the diluted specimens were added to each of the wells and allowed to react for 30 minutes at 37° C.

The wells were then washed six times with 0.05% by volume TWEEN 20 in PBS in order to remove unbound antibodies. Horseradish peroxidase conjugated goat anti-human IgG was used as a second antibody tracer to bind with the HCV antibody-peptide antigen complex formed in positive wells. 100 µL of peroxidase labeled goat anti-human IgG at a dilution of 1:1800 in 1% by volume normal goat serum, 0.05% by volume TWEEN 20 in PBS was added to each well and incubated at 37° C. for another 15 minutes.

The wells were washed six times with 0.05% by volume TWEEN 20 PBS to remove unbound antibody and reacted with 100 µL of the substrate mixture containing 0.04% by weight orthophenylenediamine (OPD) and 0.12% by volume hydrogen peroxide in sodium citrate buffer, pH 5.0. This substrate mixture was used to detect the peroxidase label by forming a colored product. Reactions were stopped by the addition of 100 µL of 1.0M $H_2SO_4$ and the $A_{492}$ nm measured.

EXAMPLE 2

Immunoreactivity of NS-3-Reactive peptides

Wells of 96-well plates were coated separately as in Example 1 for 1 hour at 37° C. with each of the indicated 17 peptides (Table 2, the sequences of which are provided in Table 1). The peptides were tested on a select panel of sera reactive with an immunodomiant conformational epitope from the NS-3 protein but not with linear epitopes from the same region. Panel members were selected as follows: HCV-seropositive plasma specimens from a commercial source (North American Biologicals, Inc) were screened for reactivity with the synthetic peptide 4 (SEQ ID NO: 4) containing conformational and linear epitopes [Mondelli (1994)]. Specimens that were reactive with Peptide 4 were further screened on pep18 [Wang (1992)]. Pep18 contains linear epitopes, but does not exhibit the conformational epitope. The selected serum panel then constituted those specimens that reacted with Peptide 4 not with Pep18.

The sums of the EIA absorbance readings at 492 nm are tabulated for each peptide (Table 2). The results show that the peptides had reactivity for a partially or fully preserved conformational epitope present in the Peptide 4 (36–103% as reactive).

EXAMPLE 3

Immunoreactivity of Core-Reactive Peptides

The immunoreactivity of peptides 22 and 26 octamer (Table 3) was determined with a group of known HCV serum samples from HCV Panel 3 containing antibodies against core in the ELISA assay format as described in Example 1. The results are shown in Table 4. The absorbances of both peptides 22 and 26 were greater than that of VIIIE (SEQ ID NO:3) on samples 3-3, 3-8 and 3-26. Peptide 26 was stronger than VIIIE on sample 3-39, and peptide 22 octamer was stronger than VIIIE on samples 3-1 and 3-41.

The immunoreactivity of peptides 26 and 37 was determined with a group of known HCV serum samples from HCV Panels 2, 3, and a seroconversion sample (serol 1-5), each containing antibodies against core, in the ELISA assay format described in Example 1 with peptide coating done at 1 µg/mL. The results shown in Table 10 indicate that peptide 37 reacts more strongly with HCV core antibodies than does peptide 26.

EXAMPLE 4

Immunoreactivity of NS-4-Reactive Peptides and NS-4/Core-Reactive Hybird Peptides The immunoreactivity of peptides 3KIIH, 27, 28, 29, and 30 (Table 5) was determined with a panel of known HCV sera from HCV panel 3 containing antibodies to the NS-4 protein in the ELISA assay format as described in Example 1. The results are shown in Table 6. All of the peptides showed stronger reactivity than the HCV-1 strain peptide 3KIIH.

A rare serum sample (NAB-2-2) was reported in U.S. Pat. No. 5,106,726 (see Table 5 therein) that reacted preferentially with the five amino terminal residues of peptide 2 (SGKPA). While this sequence is part of an epitope important for detecting samples with NS-4 reactivity, peptide 39 (Table 5), containing the sequence SGKPT, exhibited non-specific immunoreactivity, thereby leading to identification of five false-positive samples among 1000 random blood donor samples (Table 11).

It was observed that the sequence SGKPT is homologous to the highly conserved A site in helicases [Gorbalenya et al. (1989) Nucl. Acid Res. 17:4713–4730]. The HCV helicase in NS-3) has the sequence SGKST with amino acids G and K being invariant among HCV strains.

Accordingly, several peptides were synthesized (Peptides 42–43; Table 5) and analyzed for immunoreactivity with true positive HCV samples as well as lack of non-specific immunoreactivity with the false positive samples identified with peptide 39. Complete deletion of these five residues (peptide 44) eliminated the non-specific crossreactivity in the false positive samples but also decreased the reactivity with the known HCV positive sample (Table 11). Modification of the five residues (peptides 42 and 43, both having an amino-terminal sequence of NQRpS) resulted in peptides that lacked immunoreactivity with the false positive samples but had strong immunoreactivity with the known HCV positive sample NAB-2-2 (Table 11).

EXAMPLE 5

Immunoreactivity of NS-5-Reactive Peptides

The immunoreactivity of NS-5-reactive peptides (peptides 31-24; Table 7) with a panel of known HCV sera from HCV Panel 3 was assessed in the ELISA assay format as described in Example 1. The results (Table 8) indicate that these peptides exhibited similar immunoreactivity. All three of the library peptides (31, 32 and 33) containing mixtures of amino acids at fixed positions displayed immunoreactivity comparable to or greater than peptide 34 which was not a library peptide.

The immunoreactivity of an additional NS-5-reactive peptide (peptide 45; Table 7) was determined on a panel of known HCV sera from HCV Panel 3 in the ELISA assay format as described in Example 1 except that the peptides were coated at 2 µg/mL. The results (Table 12) indicate peptide 45 exhibited comparable immunoreactivity to peptide 33.

EXAMPLE 6

Detection of HCV Antibodies by Peptide Mixtures

Mixture A containing peptides 25, 29, 33 and 19, the latter peptide conjugated to BSA, was coated at a weight ratio of 2:2:0.5:8 (µg/mL) and compared to Mixture B containing peptides 25, 27 octamer, 33 and 19, the latter peptide conjugated to BSA, coated at a weight ratio of 2:2:0.5:8 (µg/mL) in the ELISA assay format described in Example 1.

Peptide 19 was conjugated to BSA using m-maleimidobenzoyl-N-hydroxysuccinimide ester (MBS) in accordance with manufacturer's recommendations (Pierce Chemical Co.) or Kitagawa et al (1976) *J. Biochem.* 79:233-236.

To assess the sensitivity and specificity of Mixtures A and B, the mixtures were assayed with a specially-selected serum panel containing panel members that had specific immunoreactivity for the HCV core, NS-3, NS-4 or NS-5 regions. This panel was prepared by screening sera against peptides VIIIE (SEQ ID NO:3) to identify core-specific sera, against peptide IIH (SEQ ID NO:2) to identify NS-4-specific sera, against Pep11(Wang, 1992) to identify NS-5-specific sera and against Peptide 4 (SEQ ID NO:4) to identify NS-3-specific sera. The so-identified sera were then diluted with normal human sera to exhibit weak to moderate reactivity on these same peptides (i.e., to provide an absorbance at 492 nm ranging from 0.3 to 2.0). The diluted samples then constituted the special sensitivity panel (Table 9) used for assay on Mixtures A and B.

The Mixtures A and B had comparable sensitivity (Table 9, upper panel).

Mixture D contained peptides 19, 33, 38, 39, 46 and 47, with peptide 19 conjugated to BSA. Peptides 39, 46, 38, 33 and 47 were coated onto ELISA plates at a weight ratio of 1.5:1:1:0.5:1 (µg/mL), respectively, for 16 hours at room temperature as described in Example 1. The peptide coating solution was aspirated from the wells and replaced with 100 µL of peptide 19-BSA conjugate at a concentration of 2.0 µg/mL in phosphate buffered saline, pH 7.2, for 1 hour at 37°. Mixture D assays were conducted as described in Example 1.

Mixture E contained peptides 19, 37, 43, 45, 46, and 47. Mixture E was coated onto ELISA plates in the same manner as Mixture D using peptides 43, 46, 37, 45 and 47 at a weight ratio of 1.5:1:1:0.5:1 (µg/mL), respectively. Mixture E assays were conducted with 25 µg/mL peptide 51 in the sample diluent.

Mixtures D and E were tested on the same panel as Mixtures A and B. The results shown in Table 9, lower panel, indicate that Mixtures D and E had an overall detection sensitivity comparable to Mixtures A and B. On two samples, core-2 and core-3, Mixtures D and E demonstrated higher sensitivity for these antibodies than Mixtures A and B.

EXAMPLE 7

Peptide Mixtures

Figure 2:
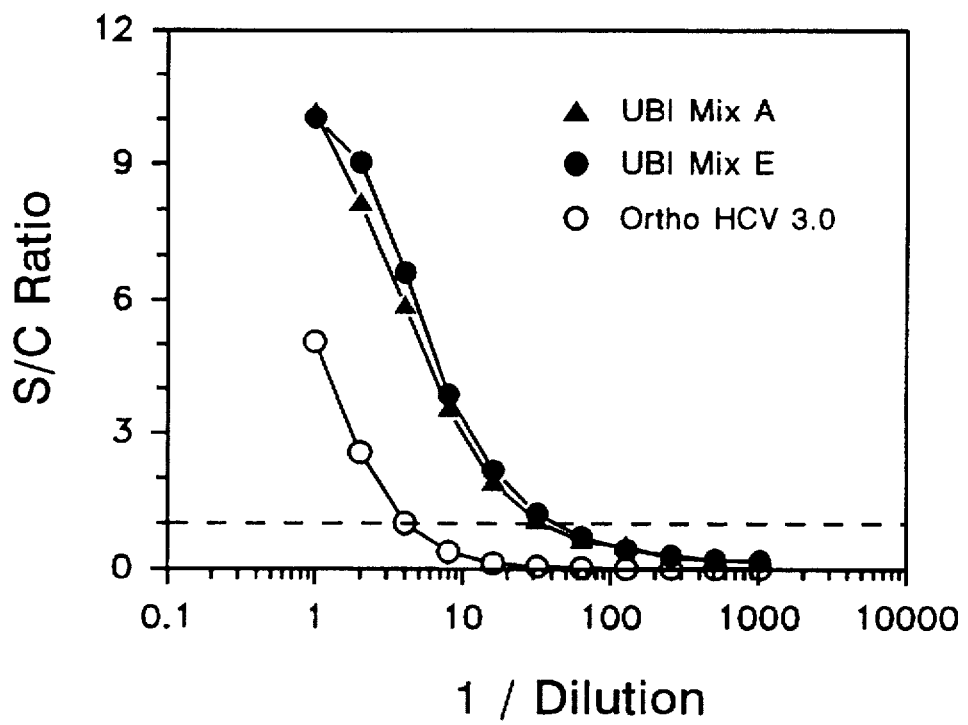
FIG. 2 graphically depicts the immunoreactivity of a dilution series of human monoclonal antibody (60H9[9] D10E6) specific for HCV NS-4 with (▲) Mixture A peptides (Example 6), (●) Mixture E peptides (Example 6) and (○) a commercially available HCV antibody detection kit (Ortho HCV 3.0).
Figure 3:
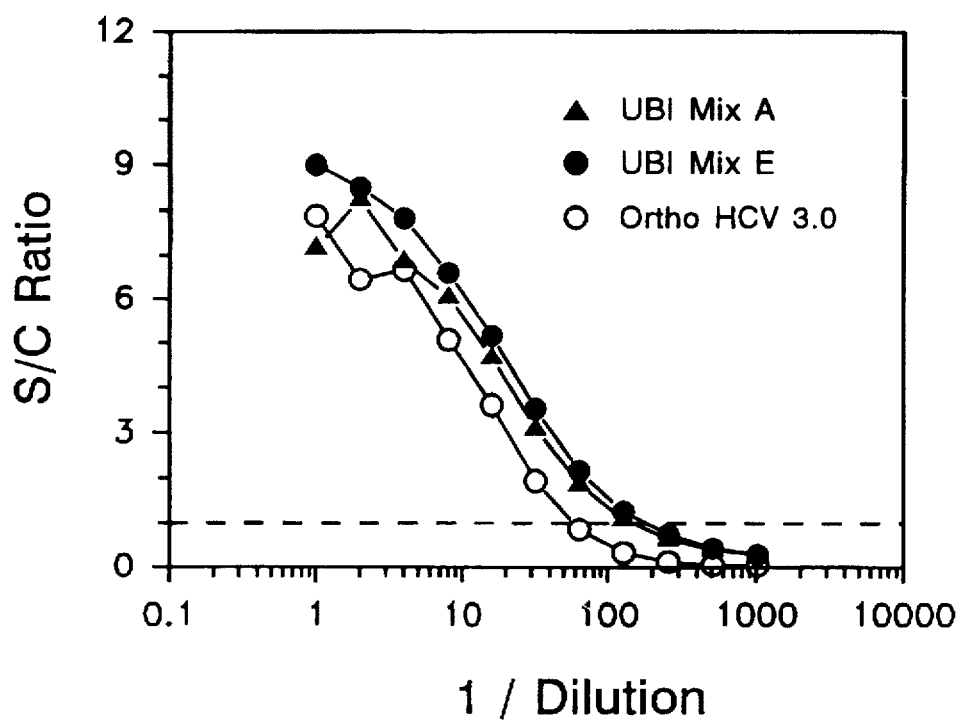
FIG. 3 graphically depicts the immunoreactivity of a dilution series of human monoclonal antibody (CM3.B6) specific for HCV NS-3 with (▲) Mixture A peptides (Example 6), (●) Mixture E peptides (Example 6) and (○) and a commercially available HCV antibody detection kit (Ortho HCV 3.0).

Mixture A (Example 6) and Mixture E (Example 6) were tested for sensitivity with a dilution series of human monoclonal antibodies specific for a) the core protein of HCV, B12.F8 [Cerino (1993)], b) the NS-4 protein of HCV, 60H|9 |D10E6 [Cerino (1991)] and c) the NS-3 protein conformational epitope, CM3.B6 [Mondelli (1994)]. The same dilution series was tested in parallel with a commercially available anti-HCV kit (Ortho HCV 3.0) composed of a mixture of recombinant proteins from the core, NS-3, NS-4 and NS-5 regions. The analytical sensitivity for detection of antibodies to all three regions was 2- to 8- fold higher using the Mixture A and E peptides over that obtained with the recombinant proteins of the commercially available kit (FIGS. 1–3).

EXAMPLE 8

Assay Efficacy Evaluation in Patient and Donor Populations

A total of 1034 samples that were confirmed positive for HCV antibodies by PCR analysis [Wang et al. (1992) *Gastroenterology* 103:609] or by Chiron RIBA® HCV 2.0 Strip Immunoblot Assay (Ortho Diagnostic Systems, Inc, Raritan, N.J.) were assayed on Mixture A ELISA in accordance with Examples 1 and 6. These samples were collected from NANBH patients with chronic or acute hepatitis, hemophiliacs, multiply transfused patients, HCV-infected patients undergoing seroconversion, and blood donors identified as previously infected with HCV. All 1034 confirmed-positive samples were positive on the Mixture A assay with a mean signal/cutoff ratio of 10.

A collection of 3154 random blood donor samples was likewise tested on the Mixture A ELISA. The specificity of this assay format was greater than 99.5% in blood donor populations. The mean signal/cutoff ratio of the samples was 0.3. Thus the confirmed positive samples had a mean signal/cutoff ratio that was 33-fold higher than that of the random blood donor samples.

A collection of 1395 random blood donor samples was tested on Mixture E as described in Example 6. The initial reactive rate was 0.4%, giving an assay specificity of 99.6%. The initially reactive samples were reassayed and all determined to be negative (although marginally so for ¾ samples). This result demonstrates the high specificity of this assay format in a donor population.

EXAMPLE 9

Immunoreactivity of an Additional NS-4 Reactive Peptide

The immunoreactivity of peptides V (SEQ ID NO:35) and 46 (Table 13) was determined with a panel of known HCV sera from HCV panel 3 containing antibodies to the NS-4 protein in the ELISA assay format as described in Example 1. The results are shown in Table 14. Peptide 46 showed comparable reactivity to the prototype HCV-1 strain peptide V (SEQ ID NO:35).

EXAMPLE 10

Spliced Peptides

Peptide 4, a control peptide containing the NS-3 conformational epitope, and spliced peptides 48, 49 and 50 were coated onto plates for ELISA assays as described in Example 1. Peptides 48-50 exhibited little to moderate reactivity with those NS-3 conformational antibodies present in the HCV Panel 3 serum samples as shown by the substantial decrease in absorbance for the majority of the samples in Table 15. Peptide 48 retained the most immunoreactivity against the linear epitope in this NS-3 region. Moreover, the three peptides reacted with sera known to give false positive results with peptide 4 in HCV assays as shown by the NYBC samples in Table 15, indicating their utility as a reagent for selective removal of the non-specific immunoreactivity associated with the NS-3 conformational epitope.

Peptides 48 and 49 were added to sample diluent at a concentration of 50 μg/mL and assayed with known HCV positive sera and known HCV false positive sera as described in Example 1 using ELISA plates coated with peptide 4. Table 16 shows that the immunoreactivity of the true positive samples (HCV Panel 3 samples) was inhibited over a range of about −26% to 23%, with the majority of samples showing a maximum of 15% inhibition and several samples showing an enhanced absorbances (allowing easier detection of truly positive sera). In contrast, Table 16 further shows that the immunoreactivity of the false positive samples (NYBC samples) was substantially inhibited by the presence of the spliced peptide in the sample diluent. At the concentrations tested, the inhibition with Peptide 48 was greater than 85% in 4/6 samples. The inhibition was titratable in a dose dependent manner for the majority of the samples.

Peptide 51 was added to sample diluent at a concentration of 25 μg/mL and assayed by ELISA on Mixture E coated onto microtiter plates as described in Example 6. When assayed in quadruplicate on two false positive samples (980421 and 820905), non-specific immunoreactivity was reduced by 90 and 94%, respectively, whereas with a known HCV NS-3 reactive sample, immunoreactivity was unchanged. Similar results were obtained on a number of false positive serum samples assayed by ELISA on Mixture D.

EXAMPLE 11

Mixtures A, D and E were assayed as described in Example 6 with three HCV confirmed-positive serum samples (by PCR, and/or RIBA). Mixture A gave false negative signals with these three samples whereas both Mixture D and E gave strongly positive signals as shown in Table 17.

Sample T14916 was selected as a rare sample that was HCV positive as confirmed by PCR testing and has been shown to contain antibodies reactive with the NS-3 and NS-5 proteins but not with the core or NS-4 proteins. The improvement in performance for sample T14916 is attributed to the addition of peptide 47 (an NS-5 reactive peptide) to Mixtures D and E. When tested alone on sample T14916, peptide 47 and its prototype peptide 36 (also known as pep12 in EP 0 468 527, published Jan. 29, 1992) had absorbances of 1.146 and 1.089, respectively, at 492 nm.

TABLE 1

NS-3-Reactive Peptides

| SEQ. ID | SEQUENCE[a,b] |
|---|---|
| 5 | KKKKAIPLEVIKGGKHLIFCHSKKKCDELAAKLVALGINAVAYYKGLDVSVIPTSGDTDALMTGYTGDFDSVIDC |
| 6 | FAvPLEvVKGGRHLIvCHTKKKCDELAAKLVALFINAVAYYRGLDVSVIPTSGDVVVVATDALMTGYTGDFDSVIDC |
| 7 | KAvPLEvVKGGRHLIvCHTKKKCDEzAALKvALGINAVAYYRGLDVSVIPTSGDVVVVATDALMTGYTGDFDSVIDCNTCV |
| 8 | KAvPLEvVKGGRHLIvCHAKKKCDEzAAKLVALGINAvAYYRGLDVSVIPTSGDVVVVATDALMTGYTGDFDSVIDCNTCV |
| 9 | KAvPLE*VKGGRHLIFCHSKKKCDELAAKLVALGINAvAYYRGLDvSVIPTSGDVVVVATDALMTGYTGDFDSVIDCNTCV |
| 10 | KAvPLE*VKGGRHLIFCHSKKKCDELAAKLVALGINAVAYYRGLDVSVIPTSGDVVVVATDALMTGYTGEFDSVIDCNTCV |
| 11 | KAvPLE*VKGGRHLIvCHSKKKCDEzAAKLVALGIQAVAYYRGLDvSVIPTSGDVVVVATDALMTGYTGDFDSvIDCNTCV |
| 12 | KAvPLE*VKGGRHLIFCHSKKKCDELAAKLVALGINAVAYYRGLDVSVIPTSGDVVVVATDAzMTGYTGDFESVIDCNTCV |
| 13 | KAvPLE*VKGGRHLIvCHSKKKCDEzAAKLVALGINAVAYYRGLDvSVIpTAGDVVVVATDAzMTGYTGDFDSVIDCNTCV |
| 14 | KAvPLE*VKGGRHLIvCHSKKKCDEzAAKLVALGzNAVAYYRGzDVSVIPTAGDVVVVATDAzMTGYTGDFDSVIDCNTCV |
| 15 | KAvPLE*VKGGRHLIvCHSKKKCDEzAAKLVALGINAVAYYRGLDvSVIPTAGDVVVVATDAzMTGYSGDFDSvIDCNTCV |
| 16 | KAvPLE*VKGGRHLIvCHSKKKCDEzAAKLVAzGINSVAYYRGLDvSVIPTAGDVVVVASDAzMTGYSGDFDSvIDCNTCV |
| 17 | KAvPLE*VKGGRHLIvCHSKKKCDEzAAKLVAzGINAIAYYRGLDvSVIPTAGDVVVVASDAzMTGYSGDFDSvIDCNTCV |
| 18 | KAvPLE*VKGGRHLIvCHSKKKCEEzAAKLVAzGINAVSYYRGLDvSVIPTAGDVVVVASDAzMTGYSGDFDSvIDCNTCV |
| 19 | KAvPLE*VKGGRHLIvCHSRKKCDEzAAKLVAzGINAVSYYRGLDvSVIPTAGDVVVVASDAzMTGYSCDFDSvIDCNTCV |
| 20 | KAvPLE*VKGGRHLIvCHSRKKCDEzAAKLVAzGINAVSYYRGLDvSVIPTAGDVVVVASDAzMTGYSGDFDSvIDCNTCV |
| 21 | KKKKAIPLEVIKGGRHLIFCHSRRRCDELAAKLVALGINAVAYYRGLDVSVIPTSGDVVVVATDALMTGYTGDFDSVIDCNTCV |

[a]The sequence in this and tables 3, 5 and 7 are provided in standard one letter amino acid codes. For unnatural amino acids, the codes are v, norvaline; p, hydroxyproline; o, ornithine and z, norleucine.
[b]The position represented by * is a library position having the amino acid distribution $V_3A_3T_1F_{.1}Y_1v_1$.

TABLE 2

Immunoreactivity of NS-3-Reactive Peptides

| Serum | 4 | 5 | 6 | 7 | 8 | 9 | 10 | 11 |
|---|---|---|---|---|---|---|---|---|
| HCV3-3 | 0.448 | 0.079 | 0.376 | 0.249 | 0.231 | 0.362 | 0.266 | 0.318 |
| HCV3-9 | 0.737 | 0.043 | 0.802 | 0.598 | 0.232 | 0.710 | 0.514 | 0.083 |
| HCV3-14 | 1.542 | 1.785 | 0.915 | 0.634 | 0.437 | 1.044 | 0.784 | 0.502 |
| HCV3-18 | 0.860 | 0.036 | 0.340 | 0.197 | 0.222 | 0.365 | 0.258 | 0.293 |
| HCV3-19 | 1.725 | 1.804 | 0.663 | 0.463 | 0.504 | 0.855 | 0.715 | 0.318 |
| HCV3-25 | 1.640 | 2.369 | 1.424 | 0.452 | 0.734 | 1.127 | 0.850 | 0.888 |
| HCV3-27 | 1.184 | 0.931 | 0.921 | 0.593 | 0.316 | 0.978 | 0.702 | 0.739 |
| HCV3-32 | 0.632 | 0.564 | 0.181 | 0.146 | 0.131 | 0.363 | 0.331 | 0.106 |
| HCV3-36 | 1.968 | 0.057 | 0.737 | 0.865 | 0.319 | 1.297 | 1.332 | 0.409 |
| HCV3-39 | 2.245 | 2.367 | 1.624 | 0.713 | 1.561 | 1.630 | 1.464 | 1.246 |
| Sum[a] | 12.981 | 10.035 | 7.983 | 4.910 | 4.687 | 8.731 | 7.216 | 4.902 |
| %[b] | 100 | 77 | 61 | 38 | 36 | 67 | 56 | 38 |

| Serum | 12 | 13 | 14 | 15 | 16 | 17 | 18 | 19 | 21 |
|---|---|---|---|---|---|---|---|---|---|
| V3-3 | 0.151 | 0.374 | 0.191 | 0.431 | 0.182 | 0.312 | 0.172 | 0.517 | 0.233 |
| V3-9 | 0.431 | 0.781 | 0.299 | 0.683 | 0.380 | 0.539 | 0.783 | 1.306 | 0.365 |
| V3-14 | 0.151 | 0.966 | 0.604 | 1.050 | 0.336 | 1.028 | 0.904 | 1.672 | 0.354 |
| V3-18 | 0.055 | 0.478 | 0.200 | 0.288 | 0.069 | 0.422 | 0.372 | 0.933 | 0.098 |
| V3-19 | 0.396 | 0.681 | 0.419 | 0.622 | 0.378 | 0.794 | 0.709 | 1.307 | 0.388 |
| V3-25 | 0.946 | 1.144 | 0.815 | 1.085 | 0.747 | 0.876 | 0.798 | 1.260 | 0.628 |
| V3-27 | 0.384 | 0.994 | 0.656 | 1.097 | 0.435 | 0.863 | 1.023 | 1.706 | 0.313 |
| V3-32 | 0.201 | 0.679 | 0.127 | 0.473 | 0.091 | 0.375 | 0.460 | 0.959 | 0.076 |
| V3-36 | 0.971 | 0.704 | 0.457 | 1.415 | 0.494 | 0.904 | 1.334 | 2.078 | 0.810 |
| V3-39 | 1.625 | 1.345 | 1.411 | 1.555 | 0.810 | 1.330 | 1.032 | 1.611 | 1.069 |
| Sum[a] | 5.311 | 8.146 | 5.179 | 8.699 | 3.922 | 7.443 | 7.587 | 13.349 | 4.334 |
| %[b] | 41 | 63 | 40 | 67 | 30 | 57 | 58 | 103 | 33 |

[a]Sum of the above absorbances at 492 nm.
[b]Percentage of immunoreactivity relative to Peptide 4.

TABLE 3

Core-Reactive Peptide

| SEQ. ID | SEQUENCE |
|---|---|
| 22 | VKFPGGGQIM—OCT |
| 23 | KKKIPKPNoKT  KRNTQRRPNDvKFPGGGNIvGGVYLVPRRGPRzGLRATRKTTERSQpRGRR—DIM |
| 24 | KKKSTIP$_9$KPQoKT$_7$KRNTNKRPQDvKFPGGGQIvGGVYLzPRRGPRzGLRAT$_9$RKTTERSQpRGRR<br>  G$_1$    N$_3$                                               P$_1$ |
| 25 | KKKSTIP$_9$KPQoKT$_7$KRNTNKRPQDvKFpGGGQIvGGVYLzPRRGPRzGLRAT$_9$RKTTERSQpRGRR<br>  G$_1$    N$_3$                                               P$_1$ |
| 26 | KKKSTIP$_9$KPQoKT$_7$KRNTNKRPQDvKFPGGGNIvGGVYLzPRRGPRzGVRAT$_9$RoTT$_1$ERSQpRGRR<br>  G$_1$    N$_3$                                                  P$_1$  A$_1$<br>                                                                                       E$_1$<br>                                                                                       K$_1$ |
| 37 | KKKSTIPKPQoKTKRNTNoRPQDVKFpGGGQvVGGVYLLpRRGPRzGvRATRKTS |
| 38 | KKKTKRNTNKRPQDVKFpGGGQvVGGVYLLpRRGPRzGvRATRKTS |

TABLE 4

Immunoreactivity of Core-Reactive Peptides

| Serum | VIIIE | 26 | 22 Octamer |
|---|---|---|---|
| HCV3-1 | 3.273 | 3.600 | 3.702 |
| HCV3-3 | 2.885 | 3.173 | 3.161 |
| HCV3-8 | 1.137 | 1.517 | 1.860 |
| HCV3-26 | 2.979 | 3.277 | 3.233 |
| HCV3-39 | 1.032 | 1.329 | 0.486 |
| HCV3-41 | 3.268 | 3.595 | 3.614 |
| Sum[a] | 14.574 | 16.491 | 16.056 |
| %[b] | 100 | 113 | 110 |

[a]Sum of the above absorbances at 492 nm.
[b]Percentage of immunoreactivity relative to peptide VIIIE.

TABLE 5

NS-4-Reactive Peptides

| SEQ. ID | SEQUENCE |
|---|---|
| 27 | IIPDREVLYM—OCT |
| 28 | KKKSGKPTIIPDREvLYREFDDMEDCSQHLPYzDQGMMLAENFKQKAVGL |
| 29 | KKKS$_8$ G$_8$K$_6$P$_8$T I$_6$ I$_6$ PDR$_8$EvLYR$_3$E$_8$FDDMEDCS$_4$ Q$_4$H$_8$L$_8$P$_8$ Y$_8$zDQ$_8$GM$_8$M$_4$L$_8$ AENF$_8$KQ$_8$KA$_8$VGLVKFPGGGNI<br>    N$_2$D$_1$R$_4$V$_1$ V$_4$V$_2$  K$_2$    Q$_5$A$_2$      A$_6$S$_6$K$_1$A$_2$A$_2$L$_2$  E$_2$  Q$_2$Q$_4$M$_1$    L$_2$ S$_2$ I$_2$<br>    Q$_1$ A$_1$   A$_2$         E$_2$                              R$_1$         R$_2$I$_1$ |
| 30 | KKKS$_8$ G$_8$K$_6$P$_8$T I$_6$ I$_6$ PDR$_8$EvLYR$_3$E$_8$FDDMEDCS$_4$ Q$_4$H$_8$L$_8$P$_8$ Y$_8$vDQ$_8$GM$_8$M$_4$L$_8$ AENF$_8$KQ$_8$KA$_8$vGLVKFPGGGNI<br>    N$_2$D$_1$R$_4$V$_1$ V$_4$V$_2$  K$_2$    Q$_5$A$_2$      A$_6$S$_6$K$_1$A$_2$A$_2$L$_2$  E$_2$  Q$_2$Q$_4$M$_1$    L$_2$ S$_2$ I$_2$<br>    Q$_1$ A$_1$   A$_2$         E$_2$                              R$_1$         R$_2$I$_1$ |
| 39 | KKKSGKPTIIPDREvLYREFDEMEDCSQHLPYIDQGMMLAENFKQKAVGL |
| 40 | KKKSGKPTIIPDREvLYREFDEMEDCSQHvPYIDQGMMLAENFKQKAVGL |
| 41 | KKKSGKPTIIPDREvLYoEFDEMEDCSQHvPYIDQGMMLAENFKQKAVGL |
| 42 | KKKNQRpSIIPDREvLYoEFDEMEDCSQHLPYIDQGMMLAENFKQKAVGL |
| 43 | KKKNQRpSIIPDREvLYoEFDEMEDCSQHvPYIDQGMMLAENFKQKAVGL |
| 44 | KKKIIPDREvLYoEFDEMEDCSQHvPYIDQGMMLAENFKQKAVGL |

TABLE 6

Immunoreactivity of NS-4-Reactive Peptides

| Serum | 3KIIH | 27 | 28 | 29 | 30 |
|---|---|---|---|---|---|
| HCV3-5  | 1.820 | 1.276 | 2.575 | 2.670 | 2.503 |
| HCV3-16 | 2.002 | 1.931 | 2.262 | 2.702 | 2.112 |
| HCV3-17 | 2.091 | 3.268 | 2.566 | 3.000 | 2.486 |
| HCV3-19 | 2.386 | 2.343 | 2.598 | 3.000 | 2.381 |
| HCV3-24 | 2.106 | 3.497 | 2.699 | 2.401 | 2.210 |
| HCV3-25 | 1.813 | 1.794 | 2.388 | 2.266 | 2.040 |
| HCV3-33 | 1.361 | 1.144 | 2.055 | 2.327 | 2.147 |
| HCV3-36 | 1.383 | 1.480 | 2.453 | 2.277 | 2.374 |
| HCV3-39 | 1.663 | 1.679 | 1.915 | 1.885 | 1.682 |
| HCV3-41 | 1.896 | 3.863 | 3.000 | 2.473 | 3.000 |
| Sum[a]  | 18.1  | 22.275 | 24.511 | 25.001 | 22.935 |
| %[b]    | 100   | 120   | 132   | 135   | 124   |

[a] Sum of the above absorbances at 492 nm
[b] Percentage of immunoreactivity relative to 3KIIH

TABLE 8

Immunoreactivity of NS-5-Reactive Peptides

| Serum | 31 | 32 | 33 | 34 |
|---|---|---|---|---|
| HCV3-1  | 1.974 | 2.155 | 2.215 | 2.097 |
| HCV3-5  | 0.802 | 0.906 | 0.937 | 0.687 |
| HCV3-17 | 1.946 | 2.183 | 2.339 | 2.742 |
| HCV3-19 | 1.920 | 2.023 | 2.051 | 1.781 |
| HCV3-33 | 1.191 | 1.385 | 1.583 | 0.256 |
| HCV3-41 | 1.254 | 0.806 | 1.885 | 1.877 |
| Sum[a]  | 9.087 | 9.458 | 11.01 | 9.440 |
| %[b]    | 96    | 100   | 117   | 100   |

[a] Sum of the above absorbances at 492 nm.
[b] Percentage of immunoreactivity relative to Peptide 32.

TABLE 7

NS-5-Reactive Peptides

| SEQ. ID | SEQUENCE |
|---|---|
| 31 | DYNPP$_8$LvET$_5$WKK$_4$PEYE$_5$PP$_9$ V$_8$vH$_8$GCP$_8$LPP$_9$pK$_8$S$_4$ P$_8$PV$_5$pPPRK$_4$K$_7$RT$_9$<br>    L$_1$   S$_4$   D$_4$   V$_4$ A$_1$T$_2$ L$_1$   A$_2$   S$_1$ P$_1$A$_4$T$_2$ L$_4$     R$_6$R$_3$ A$_1$<br>    V$_1$   P$_1$   R$_2$   Q$_1$       A$_1$                R$_1$K$_1$   T$_1$<br>                                                            Q$_1$ |
| 32 | PDYNPP$_8$LvET$_5$WKK$_4$PEYE$_5$PP$_9$ V$_8$vH$_8$GCP$_8$LPP$_9$pK$_8$S$_4$ P$_8$PV$_5$pPPRK$_4$K$_7$RT$_9$<br>    L$_1$   S$_4$   D$_4$   V$_4$ A$_1$T$_2$ L$_1$   A$_2$   S$_1$ P$_1$A$_4$T$_2$ L$_4$     R$_6$R$_3$ A$_1$<br>    V$_1$   P$_1$   R$_2$   Q$_1$       A$_1$                R$_1$K$_1$   T$_1$<br>                                                            Q$_1$ |
| 33 | AoPDYNPP$_8$LvET$_5$WKK$_4$PEYE$_5$PP$_9$ V$_8$vH$_8$GCP$_8$LPP$_9$pK$_8$S$_4$ P$_8$PV$_5$pPPRK$_4$K$_7$RT$_9$<br>    L$_1$   S$_4$   D$_4$   V$_4$ A$_1$T$_2$ L$_1$   A$_2$   S$_1$ P$_1$A$_4$T$_2$ L$_4$     R$_6$R$_3$ A$_1$<br>    V$_1$   P$_1$   R$_2$   Q$_1$       A$_1$                R$_1$K$_1$   T$_1$<br>                                                            Q$_1$ |
| 34 | PLvETWKKPEYEPPVvHGCPLPPpKSPPVPPpRKKRT—DIM |
| 45 | AoPDYNPPLvETWKKPEYEPPVvHGCPLPPpKSPPVpPPRKKRT |

TABLE 9

Sensitivity and Specificity of Peptide Mixtures

| Sample[a] | Mixture A | | Mixture B | |
|---|---|---|---|---|
| | Abs | Ratio[b] | Abs | Ratio[b] |
| Core-1 | 1.099 | 2.57 | 1.085 | 2.67 |
| Core-2 | 2.444 | 5.72 | 2.210 | 5.44 |
| Core-3 | 1.646 | 3.85 | 1.747 | 4.30 |
| NS3-1 | 0.664 | 1.55 | 0.642 | 1.58 |
| NS3-2 | 1.557 | 3.65 | 1.757 | 4.33 |
| NS4/NS3-1 | 1.902 | 4.45 | 1.819 | 4.48 |
| NS4-1 | 1.404 | 3.29 | 0.658 | 1.62 |
| Neg-1 | 0.163 | 0.38 | 0.180 | 0.44 |
| Neg-2 | 0.170 | 0.40 | 0.191 | 0.47 |
| Neg-3 | 0.136 | 0.32 | 0.152 | 0.37 |

| Sample[a] | Mixture D | | Mixture E | |
|---|---|---|---|---|
| | Abs | Ratio[b] | Abs | Ratio[b] |
| Core-1 | 0.691 | 2.49 | 1.030 | 2.79 |
| Core-2 | 2.249 | 8.10 | 2.749 | 7.44 |
| Core-3 | 1.734 | 6.24 | 2.044 | 5.53 |
| NS3-1 | 0.435 | 1.57 | 0.813 | 2.20 |
| NS3-2 | 1.496 | 5.39 | 1.748 | 4.73 |
| NS4/NS3-1 | 1.908 | 6.87 | 1.746 | 4.72 |
| NS4-1 | 1.008 | 3.63 | 1.406 | 3.80 |
| Neg-1 | 0.073 | 0.26 | 0.151 | 0.41 |
| Neg-2 | 0.069 | 0.25 | 0.097 | 0.26 |
| Neg-3 | 0.075 | 0.27 | 0.128 | 0.35 |

[a]Panel members selected as described in Example 7, Neg is normal human serum known to be negative for HCV antibodies.
[b]Ratio is the absorbance over the cutoff value. Cutoff value were as follows: Mixture A, 0.427; Mixture B, 0.406; Mixture D, 0.278; and Mixture E, 0.370.

TABLE 10

Immunoreactivity of Core-Reactive Peptides

| Serum | 26 | 37 |
|---|---|---|
| Serol 1-5 | 0.382 | 0.722 |
| HCV 3-12 | 1.490 | 1.799 |
| HCV 3-15 | 0.524 | 1.379 |
| HCV 3-16 | 0.481 | 1.538 |
| HCV 2-22 | 1.561 | 1.521 |
| HCV 2-32 | 2.402 | 2.737 |
| HCV 2-35 | 0.094 | 0.181 |
| Sum[a] | 6.934 | 9.877 |

[a]Sum of the above absorbances at 492 nm.

TABLE 11

Elimination of False Positives with NS-4 Reactive Peptides

| Serum | 39 | 44 | 42 | 43 |
|---|---|---|---|---|
| HCV Positive | | | | |
| NAB-2-2 | 0.623 | 0.366 | 0.645 | 0.819 |
| False Positive | | | | |
| 18-109 | 0.726 | 0.103 | 0.088 | 0.057 |
| 18-425 | 0.607 | 0.072 | 0.075 | 0.136 |
| 18-955 | 0.772 | 0.063 | 0.077 | 0.052 |
| 18-1936 | 0.892 | 0.058 | 0.066 | 0.059 |
| 18-1006 | 0.765 | 0.055 | 0.055 | 0.051 |

TABLE 12

Immunoreactivity of NS-5-Reactive Peptide

| Serum | 33 | 45 |
|---|---|---|
| HCV 3-1 | >3 | 2.826 |
| HCV 3-5 | 2.800 | 2.673 |
| HCV 3-11 | 1.357 | 1.951 |
| HCV 3-13 | 0.853 | 1.001 |
| HCV 3-14 | 2.769 | 2.877 |
| HCV 3-15 | 0.065 | 0.062 |
| HCV 3-17 | 2.998 | 2.842 |
| HCV 3-19 | >3 | 2.759 |
| HCV 3-24 | 0.530 | 0.515 |
| HCV 3-25 | 1.517 | 2.219 |
| HCV 3-26 | 2.152 | 2.342 |
| HCV 3-29 | 0.161 | 0.220 |
| HCV 3-33 | 2.697 | 2.219 |
| HCV 3-41 | 2.843 | 2.666 |
| JP-7 | 0.946 | 1.120 |
| JP-9 | 0.181 | 0.508 |

TABLE 13

Additional Reactive Peptides

| SEQ. ID | Reactivity[a] | SEQUENCE |
|---|---|---|
| 46 | NS-4 | KQKALGLzQTASoQAEVIApAVQTNWQRLETFWAoHMWNF |
| 47 | NS-5 | KATCTANoDSPDAELvEANLLWRNEMGGNTIoVESENKVvILDSFDPzVAEEDER |
| 48 | NonSp | KKKCDELAAKLVATDALMTGYTGDFDSVIDCNTCV |
| 49 | NonSp | GRHLIFCHSKKKCDELAAKLVATDALMTGYTGDFDSVIDCNTCV |
| 50 | NonSp | KAIPLEVIKGGRHLIFCHSKKKCDELAAKLVATDALMTGYTGDFDSVIDCNTCV |
| 51 | NonSp | KKKCDEzAAKLVATDAzMTGYTGEFDSvIDCNTCV |

[a]Reactivity indicates that peptides 46 and 47 are specific for the antibodies directed against HCS NS-4 and NS-5 proteins, respectively. NonSp indicates the spliced peptides that block non-specific immunoreactivity associated with the NS-3 conformational epitope in peptide 4.

TABLE 14

Immunoreactivity of NS-4 Reactive Peptides Related to Peptide V

| Serum | 35 | 46 |
|---|---|---|
| HCV3-3 | 0.578 | 0.682 |
| HCV3-18 | 0.059 | 0.055 |
| HCV3-27 | 1.251 | 1.513 |
| HCV3-31 | 1.718 | 1.915 |
| HCV3-37 | 0.112 | 0.142 |
| 95-100A* | 0.515 | 0.528 |

*Because of available sample volume, this sample was dilu 1:4 before assay. The absorbance value reported is as measured on the diluted serum.

TABLE 15

Specificity of Spliced Peptides

| Sera | 4 | 48 | 49 | 50 |
|---|---|---|---|---|
| BLK | 0.052 | 0.053 | 0.055 | 0.056 |
| NRC | 0.027 | 0.043 | 0.054 | 0.052 |
| WRC | 0.092 | | | |
| SRC | 0.380 | | | |
| HCV 3-13 | Over | 0.584 | 0.107 | 0.071 |
| HCV 3-14 | 1.711 | 0.750 | 0.110 | 0.069 |
| HCV 3-16 | 1.751 | 0.749 | 0.095 | 0.050 |
| HCV 3-17 | 2.049 | 1.714 | 0.173 | 1.331 |
| HCV 3-20 | 2.581 | 1.303 | 0.145 | 0.034 |
| HCV 3-21 | 2.724 | 0.410 | 0.121 | 0.123 |
| HCV 3-24 | 2.429 | 1.678 | 0.953 | 1.342 |
| HCV 3-28 | 2.924 | 0.725 | 0.135 | 0.086 |
| HCV 3-29 | 2.424 | 1.021 | 0.117 | 0.040 |
| HCV 3-30 | 2.607 | 1.008 | 0.011 | 0.045 |
| HCV 3-34 | 1.266 | 0.380 | 0.055 | 0.049 |
| HCV 3-38 | 2.373 | 0.800 | 0.580 | 0.695 |
| HCV 3-39 | 2.219 | 0.781 | 0.148 | 0.066 |
| HCV 3-40 | 2.706 | 1.678 | 0.429 | 0.298 |
| HCV 3-41 | 2.299 | 1.158 | 0.137 | 0.058 |
| NYBC-13-346 | 0.505 | 0.652 | 0.603 | 0.734 |
| 525 | 1.867 | 2.333 | 2.546 | 2.109 |
| 574 | 0.246 | 2.458 | 2.298 | 2.292 |
| 715 | 0.238 | 0.576 | 0.558 | 0.590 |
| 854 | 0.255 | 0.721 | 0.730 | 0.806 |
| 869 | 0.989 | 0.901 | 1.000 | 1.130 |

TABLE 16

NS-3 Inhibition Study

| Sera | Control Abs | 48 Abs | 48 % I | 49 Abs | 49 % I |
|---|---|---|---|---|---|
| BLK | 0.052 | 0.052 | | | |
| NRC | 0.035 | 0.035 | | 0.035 | |
| WRC | 0.153 | 0.153 | | 0.094 | |
| SRC | 0.485 | 0.485 | | 1.290 | |
| HCV-3-13 | 3.000 | 2.548 | 15.1 | 3.000 | -8.2 |
| HCV 3-14 | 1.653 | 1.461 | 11.6 | 1.952 | 5.3 |
| HCV 3-16 | 1.579 | 1.546 | 2.1 | 1.880 | 6.5 |
| HCV 3-17 | 1.566 | 1.311 | 16.3 | 1.576 | 7.7 |
| HCV 3-20 | 2.391 | 3.000 | -25.5 | 2.295 | 23.5 |
| HCV 3-21 | 2.636 | 2.597 | 1.5 | 2.676 | -7.6 |
| HCV 3-24 | 2.379 | 2.855 | -20.0 | 2.470 | 17.7 |
| HCV 3-28 | 2.792 | 2.615 | 6.3 | 2.280 | 14.8 |
| HCV 3-29 | 2.454 | 2.687 | -9.5 | 2.470 | 17.7 |
| HCV 3-30 | 2.559 | 2.705 | -5.7 | 2.564 | 14.5 |
| HCV 3-34 | 1.185 | 0.977 | 17.6 | 0.921 | 12.2 |
| HCV 3-38 | 3.000 | 3.000 | 0.0 | 2.551 | -4.1 |
| HCV 3-39 | 1.984 | 1.999 | -0.8 | 2.336 | -4.2 |
| HCV 3-40 | 2.399 | 2.677 | -11.6 | 3.000 | -15.7 |
| HCV 3-41 | 2.731 | 2.633 | 3.6 | 2.909 | -9.2 |
| NYBC-13-346 | 0.503 | 0.066 | 86.9 | 0.086 | 84.5 |
| 525 | 1.886 | 0.582 | 69.1 | 1.536 | 21.7 |
| 574 | 0.619 | 0.042 | 93.2 | 0.857 | 39.3 |
| 715 | 0.378 | 0.054 | 85.7 | 0.079 | 79.8 |
| 854 | 0.561 | 0.125 | 77.7 | 0.347 | 42.4 |
| 869 | 0.917 | 0.076 | 91.7 | 0.113 | 87.5 |

TABLE 17

| Sera | Mixtures* A | D | E |
|---|---|---|---|
| 95-100A | 0.50 | 3.4 | —[b] |
| T14916 | 0.18 | 4.9 | 6.54 |
| 94/1492 | 0.21 | 1.8 | 1.13 |

*The values reported are signal to cut-off ratios.
[b]—, Assay not performed because of insufficient sample.

We claim:

1. A peptide composition comprising Mixture E wherein Mixture E consists essentially of Peptides 19, 37, 43, 45, 46 and 47 (SEQ ID NOS:19, 37, 43, 45, 46 and 47).

2. A method of detecting hepatitis C, HCV, antibodies or diagnosis of HCV infection in a subject which comprises
   (i) providing a peptide composition according to claim 1;
   (ii) contacting an effective amount of said peptide composition with a serum, tissue, tissue extract or a body fluid from a subject in an immunoassay procedure for a time sufficient to form a complex between said peptide composition and any antibody in said serum, said tissue, said tissue extract or said fluid, and
   (iii) subjecting said complex to a detecting means, thereby detecting HCV antibodies or diagnosing HCV infection in the subject.

3. The method of claim 2 wherein said immunoassay procedure is an enzyme-linked immunoadsorbent, ELISA, assay; a sandwich assay; a passive hemagglutination, PHA, assay.

4. A kit for detection of HCV antibodies or diagnosis of HCV infection comprising a first container having a solid phase coated with the peptide composition of claim 1.

5. An ELISA test kit for detection of HCV antibodies or diagnosis of HCV infection comprising
   (a) a container having a solid phase coated with the peptide composition of claim 1;
   (b) a negative control sample;
   (c) a positive control sample;
   (d) specimen diluent; and
   (e) antibodies to human IGg, said antibodies labeled with a reporter molecule.

6. An ELISA test kit for detection of HCV antibodies or diagnosis of HCV infection comprising
   (a) a solid-phase coated with the peptide composition of claim 1; and
   (b) a specimen diluent comprising a spliced peptide selected from the group consisting of SEQ ID NOS: 48–51 or selected from the group consisting of an analog of SEQ ID NOS:48–51 having an amino acid sequence of the corresponding NS-3 region of an isolate/strain of HCV in soluble form.

7. The ELISA test kit of claim 6 further comprising
   (c) a negative control sample;
   (d) a positive control sample; and
   (e) antibodies to human IgG, said antibodies labeled with a reporter molecule.

8. The ELISA test kit of claim 7, wherein said spliced peptide is SEQ ID NO:51.

9. A method of detecting HCV antibodies or diagnosis of HCV infection in a subject which comprises
   (i) providing a first peptide composition Mixture E, wherein Mixture E consists essentially of Peptides 19, 37, 43, 45, 46, and 47;
   (ii) contacting an effective amount of said first peptide composition with a serum, tissue, tissue extract or a body fluid from the subject in the presence of or after contacting with an effective amount of a second soluble peptide composition comprising a linear spliced peptide derived from the NS-3 region of HCV, said linear spliced peptide selected from the group consisting of SEQ ID NOS:48–51 and wherein the C terminal amino acid of said linear spliced peptide is a carboxylic acid or carboxylic amide or an analog of SEQ ID NOS:48–51, said analog having an amino acid sequence of the corresponding NS-3 region of an isolate/strain of HCV, in an immunoassay procedure for a time sufficient to form a complex between said first peptide composition and any antibody in said serum, said tissue, said tissue extract or said fluid, and
   (iii) subjecting said complex to a detecting means, thereby detecting HCV antibodies or diagnosing HCV infection in the subject.

10. The method of claim 9 wherein said immunoassay procedure is an ELISA assay, a sandwich assay or a PHA assay.

11. The method claim 9 wherein said immunoassay procedure is an ELISA assay, a sandwich assay or a PHA assay.

12. The method of claim 9 wherein said spliced peptide is polymerized to form a polymerized spliced peptide.

13. The method of claim 12 wherein said polymerized spliced peptide is represented by the formula:

(peptide)$_2$X, (peptide)$_4$X$_2$X, or (peptide)₈X₄X₂X wherein X is an amino acid or an amino acid analog having two amino groups and one carboxyl group, each group capable of forming a peptide bond linkage.

14. The method of claim 9 comprising a linear spliced peptide wherein the C terminal amino acid of said peptide is a carboxylic acid or carboxylic amide, wherein said peptide blocks non-specific reactivity of NS-3 conformational epitopes in HCV immunoassays, and wherein said peptide substantially retains the frame of the 35 amino acid prototype sequence of SEQ ID NO:48 and has the following substituted positions:

position 7: norleucine; position 17 : norleucine; position 24: glutamate; and position 28: norvaline.

15. The method of claim 14, wherein said spliced peptide is SEQ ID NO:51.

16. The method of claim 15 wherein said spliced peptide is polymerized to form a polymerized spliced peptide.

17. The method of claim 16 wherein said polymerized spliced peptide is represented by the formula:

(peptide)₂X, (peptide)₄X₂X, (peptide)₈X₄X₂X wherein X is an amino acid or an amino acid analog having two amino groups and one carboxyl group, each group capable of forming a peptide bond linkage.

18. The method of claim 14 wherein said spliced peptide is polymerized to form a polymerized spliced peptide.

19. The method of claim 18 wherein said polymerized spliced peptide is represented by the formula:

(peptide)₂X, (peptide)₄X₂X, or (peptide)₈X₄X₂X wherein X is an amino acid or an amino acid analog having two amino groups and one carboxyl group, each group capable of forming a peptide bond linkage.

20. A method of detecting HCV antibodies or diagnosis of HCV infection in a subject which comprises
  (i) providing a first peptide composition comprising Peptides 37, 43, 45, 46, and 47 and a peptide selected from the group consisting of
    (a) peptide 4 (SEQ ID NO:4);
    (b) an analog peptide having an amino acid sequence of a strain/isolate of HCV in a region corresponding to said peptide 4;
    (c) a linear peptide wherein the C terminal amino acid of said peptide is a carboxylic acid or carboxylic amide, wherein said peptide is specifically immunoreactive with HCV antibodies, and wherein said peptide substantially retains the frame of the 81 amino acid prototype sequence of SEQ ID NO:4, which is immunoreactive with HCV NS-3 antibodies and which has the following substituted or degenerate positions:
      position 3: norvaline; position 7: norvaline or Val:Ala:Thr:Phe:Tyr:Nvl at 3:3:1:1:1:1 ratio; position 8: valine or norvaline; position 16: norvaline; position 20: arginine; position 26: norleucine; position 33: norleucine; position 39: serine; position 46: norvaline; position 52: alanine; position 60: serine; position 63: norleucine; position 68: serine; and position 74: norvaline; and
    (d) any one of peptides 5–18, 20, 21 (SEQ ID NOS:5–18, 20, 21).
  (ii) contacting an effective amount of said first peptide composition with a serum, tissue, tissue extract or a body fluid from the subject in the presence of or after contacting with an effective amount of a second soluble peptide composition comprising a linear spliced peptide derived from the NS-3 region of HCV, said linear spliced peptide selected from the group consisting of SEQ ID NOS:48–51 and wherein the C terminal amino acid of said linear spliced peptide is a carboxylic acid or carboxylic amide or an analog of SEQ ID NOS:48–51, said analog having an amino acid sequence of the corresponding NS-3 region of an isolate/strain of HCV, in an immunoassay procedure for a time sufficient to form a complex between said first peptide composition and any antibody in said serum, said tissue, said tissue extract or said fluid, and
  (iii) subjecting said complex to a detecting means, thereby detecting HCV antibodies or diagnosing HCV infection in the subject.

21. The method of claim 20, wherein said first peptide composition is conjugated to a carrier.

22. The method of claim 20, wherein said first peptide composition is polymerized to form a polymerized peptide.

23. The method of claim 22 wherein said polymerized peptide is represented by the formula:

(peptide)₂X, (peptide)₄X₂X, or (peptide)₈X₄X₂X wherein X is an amino acid or an amino acid analog having two amino groups and one carboxyl group, each group capable of forming a peptide bond linkage.

24. A kit for detection of HCV antibodies or diagnosis of HCV infection comprising a first container containing Mixture E wherein the peptides are affixed to a solid phase, and a second container containing a specimen diluent comprising a spliced peptide selected from the group consisting of SEQ ID NOS: 48–51 or selected from the group consisting of an analog of SEQ ID NOS:48–51 having amino acid sequence of the corresponding NS-3 region of an isolate/strain of HCV.

25. The kit of claim 24 wherein said kit is an ELISA assay kit, a sandwich assay kit or PHA assay kit.

* * * * *